United States Patent [19]

Yamamoto et al.

[11] Patent Number: 4,910,315

[45] Date of Patent: * Mar. 20, 1990

[54] 5,6-DIHYDROIMIDAZO[2,1-B]THIAZOLE-2-CARBOXAMIDE DERIVATIVES OF SALTS THEREOF

[75] Inventors: Itaru Yamamoto, Okayama; Kenji Matsunari, Fujieda; Koyata Nitta, Tokyo; Kensuke Shibata; Noriyasu Takayanagi, both of Shizuoka, all of Japan

[73] Assignees: Kumiai Chemical Industry Co., Tokyo; Toyo Jozo Co., Ltd., Shizuoka, both of Japan

[ * ] Notice: The portion of the term of this patent subsequent to Apr. 5, 2005 has been disclaimed.

[21] Appl. No.: 242,171

[22] Filed: Sep. 9, 1988

Related U.S. Application Data

[63] Continuation of Ser. No. 853,204, Apr. 17, 1986, abandoned.

[30] Foreign Application Priority Data

Apr. 22, 1985 [JP] Japan ................................. 60-85679
Apr. 25, 1985 [JP] Japan ................................. 60-89506
Apr. 25, 1985 [JP] Japan ................................. 60-89507

[51] Int. Cl.$^4$ .......................................... C07D 513/04
[52] U.S. Cl. ..................................................... 548/154
[58] Field of Search ............................................ 548/154

[56] References Cited

U.S. PATENT DOCUMENTS 4,103,016  7/1978  Moses ................................. 548/154
4,556,609  12/1985  Nishio ................................ 514/368

Primary Examiner—Robert Gerstl
Attorney, Agent, or Firm—Oblon, Spivak, McClelland, Maier & Neustadt

[57] ABSTRACT 5,6-dihydroimidazo[2,1-b]thiazole-2-carboxamide derivatives represented by the following general formula [I]

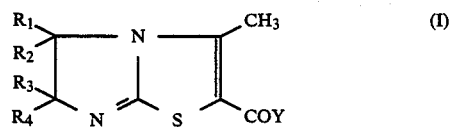

wherein $R_1$, $R_2$, $R_3$ and $R_4$ are either the same or different and mean individually a hydrogen atom or lower alkyl group, Y denotes a specific phenyl-containing substituted amino group, and their salts. These compounds have excellent immuno-modulating activities.

10 Claims, No Drawings

5,6-DIHYDROIMIDAZO[2,1-B]THIAZOLE-2-CARBOXAMIDE DERIVATIVES OF SALTS THEREOF

This is a continuation of application Ser. No. 853,204, filed Apr. 17, 1986, now abandoned.

BACKGROUND OF THE INVENTION (1) Field of the Invention:

This invention relates to novel 5,6-dihydroimidazo[2,1-b]thiazole-2-carboxamide derivatives, and more specifically to 5,6-dihydroimidazo[2,1-b]thiazole-2-carboxamide derivatives having excellent immuno-modulating activities.

(2) Description of the Prior Art:

A number of compounds having the imidazothiazole skeleton have heretofore been synthesized. For example, an imidazo[2,1-b]thiazole derivative (levamisole) represented by the following formula:

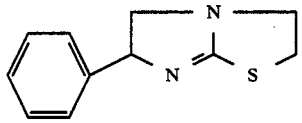

has been reported to have some immuno-modulating activities (German Offenlegungsschrift No. 23 40 632). It has also been reported that certain anti-inflammatory activities are exhibited by imidazo[2,1-b]thiazole derivatives represented by the following formula:

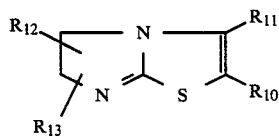

wherein $R_{10}$ means a $C_1$–$C_3$-alkylsulfonyl or

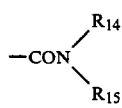

group, $R_{14}$ and $R_{15}$ being independently a hydrogen atom or a monofluorophenyl, trifluoromethylphenyl or trimethylphenyl group with a proviso that when either one of $R_{14}$ and $R_{15}$ is a hydrogen atom the other one is other than a hydrogen atom or being coupled to each other together with the associated nitrogen atom to form a 1-(2,3-dimethyl)pyrrolidinyl group, $R_{11}$ denotes a $C_1$–$C_3$-alkyl or phenyl group, and $R_{12}$ and $R_{13}$ stand independently for a hydrogen atom or a $C_1$–$C_4$-alkyl group [U.S. Pat. No. 4,224,334; J. Med. Chem. 24, 604–609 (1981)]; and by 5,6-dihydroimidazo[2,1-b]thiazole derivatives represented by the following formula:

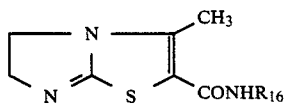

wherein $R_{16}$ means a substituted or unsubstituted phenyl or naphthalyl group (Japanese Patent Laid-Open No. 169490/1982).

SUMMARY OF THE INVENTION

An object of this invention is to provide certain imidazo[2,1-b]thiazole derivatives having excellent immuno-modulating activities.

With the foregoing in view, the present inventors synthesized a variety of imidazo[2,1-b]-thiazole derivatives and their physiological activities were investigated. As a result, it has been found that novel 5,6-dihydroimidazo[2,1-b]thiazole-2-carboxamide derivatives having certain specific substituents and represented by the above general formula (I) have excellent immuno-modulating activities, leading to completion of this invention.

In one aspect of this invention, there is thus provided a 5,6-dihydroimidazo[2,1-b]thiazole-2-carboxamide derivative represented by the following general formula [I]

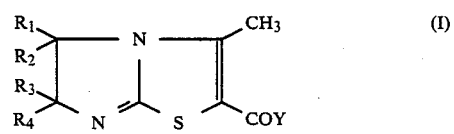

wherein $R_1$, $R_2$, $R_3$ and $R_4$ are either the same or different and mean individually a hydrogen atom or lower alkyl group, Y denotes a group of the following formula:

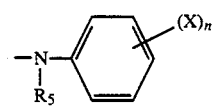

wherein $R_5$ means a lower alkyl group, X denotes a hydrogen or halogen atom or a trifluoromethyl, lower alkyl, lower alkoxy or nitro group, n stands for an integer of 0–5, and when n is greater than 1, Xs are either the same or different;

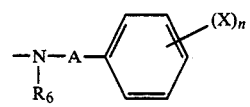

wherein A means a lower alkylene group which may be branched, $R_6$ denotes a hydrogen atom or a lower alkyl or cycloalkyl group, and X and n have the same meaning as defined above;

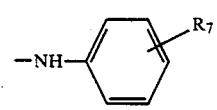

wherein $R_7$ means a hydrogen, chlorine, bromine or iodine atom or a lower alkyl, lower alkoxy or nitro group; or

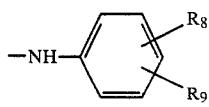

wherein $R_8$ means a halogen atom or a lower alkoxy or trifluoromethyl group and $R_9$ denotes a halogen atom or a hydroxyl, lower alkoxy or trifluoromethyl group), with a proviso that at least one of $R_1$, $R_2$, $R_3$ and $R_4$ is a methyl group when the group Y is

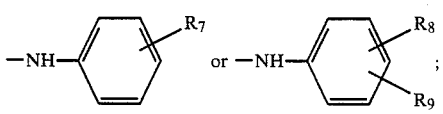

or a salt thereof.

As salts of the 5,6-dihydroimidazo[2,1-b]-thiazole-2-carboxamide derivatives in the present invention, may be mentioned their pharmacologically acceptable salts, for example, their inorganic and organic acid salts such as hydrochlorides, sulfates, carbonates, nitrates, hydrobromides, phosphates, sulfonates, acetates, oxalates, tartrates, citrates, malates, glutamates, aspartates, etc. The compounds (I) of this invention and their salts may contain water of crystallization. Their hydrates are all embraced within the scope of this invention.

The compounds (I) of this invention and their salts have excellent immuno-modulating activities and can hence be used, as preventive and therapeutic medicines for immunological disease, for the treatment and prevention of autoimmune diseases such as chronic rheumatoid arthritis, systemic lupus erythematodes, collagen disease, chronic nephritis and autoimmunohemolytic anemia, delayed-type and immediate-type allergic diseases, malignant tumors and serious infectious diseases by way of example.

The above and other objects, features and advantages of this invention will become apparent from the following description and the appended claims.

DETAILED DESCRIPTION OF THE INVENTION AND PREFERRED EMBODIMENTS

The compounds (I) of this invention may be roughly divided into the following three groups (Ia)–(Ic):

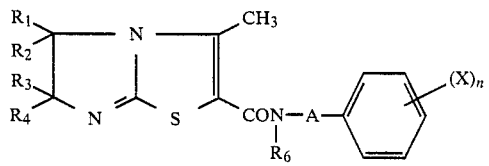

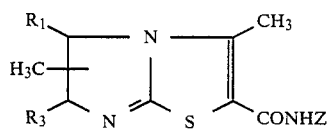

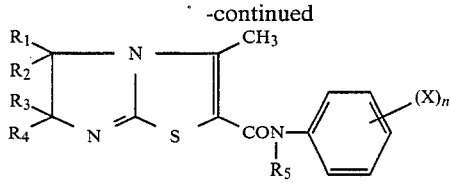

wherein Z means a group of the following formula:

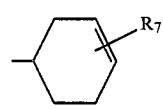

wherein $R_7$ means a hydrogen, chlorine, bromine or iodine atom or a lower alkyl, lower alkoxy or nitro group; or

wherein $R_8$ means a halogen atom or a lower alkoxy or trifluoromethyl group and $R_9$ denotes a halogen atom or a hydroxyl, lower alkoxy or trifluoromethyl group; and and $R_1$-$R_6$, A, X and n have the same meaning as defined above.

The term "lower" as used herein such as "lower alkylene", "lower alkoxy" and the like means 1-5 carbon atoms.

Among the compounds (Ia), those represented by the following formula (Ia-1) are preferred:

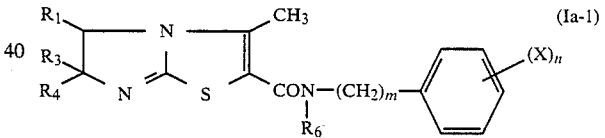

wherein m stands for an integer of 1-3, and $R_1$, $R_3$, $R_4$, $R_6$, X and n have the same meaning as defined above.

Of the compounds (Ia-1), particularly-preferred compounds are those having the formula (Ia-1) in which $R_1$, $R_3$, $R_4$ and $R_6$ mean individually a hydrogen atom or methyl group and X denotes a halogen atom or trifluoromethyl group.

Among the compounds (Ia-1), still preferred compounds are represented by the following formulae respectively.

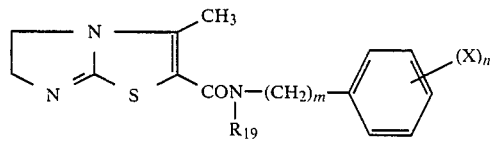

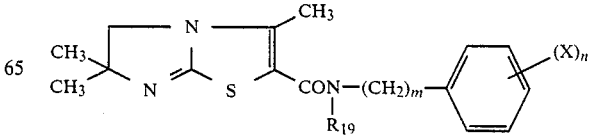

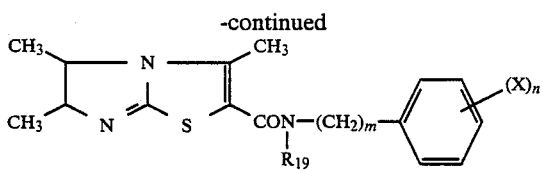

wherein $R_{19}$ means a hydrogen atom or alkyl group having 1-3 carbon atoms, m stands for an integer of 1-3, and X and n have the same meaning as defined above.

Among the compounds (Ib), those represented by he following formula (Ib-1) are preferred:

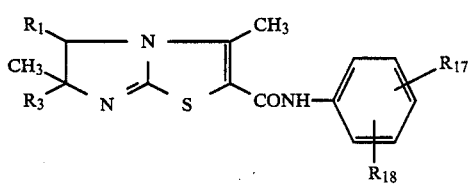

wherein $R_{17}$ and $R_{18}$ may be either the same or different and mean individually a hydrogen, chlorine or iodine atom or trifluoromethyl group, with a proviso that $R_{18}$ is other than a trifluoromethyl group when $R_{17}$ is a hydrogen atom, and $R_1$ and $R_3$ have the same meaning as defined above. Of these, those represented by the formula (Ib-1) in which $R_1$ and $R_3$ are individually a hydrogen atom or methyl group are especially preferred.

Among the compounds (Ic), those represented by the following formula (Ic-1) are preferred:

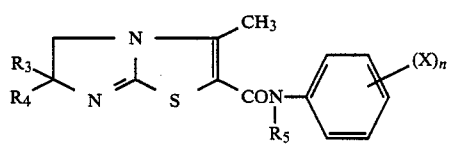

wherein $R_3$, $R_4$, $R_5$, X and n have the same meaning as defined above. Of these, particularly-preferred compounds are those represented by the formula (Ic-1) in which $R_3$ and $R_4$ are individually a hydrogen atom or methyl group, $R_5$ denotes a methyl or ethyl group, and X stands for a halogen atom or trifluoromethyl group.

The compounds (I) of this invention can each be prepared, for example, by reacting an imidazolidine-2-thione represented by the following formula (III) with an amid represented by the following formula (II) in accordance with the following reaction formula:

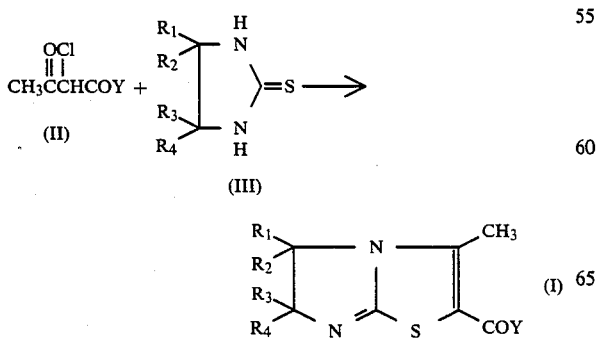

wherein $R_1$, $R_2$, $R_3$, $R_4$ and Y have the same meaning as defined above.

It is preferable to conduct the above reaction in a suitable inert solvent. As an illustrative solvent useful in the above reaction, may be mentioned benzene, toluene, xylene, acetone, methyl ethyl ketone, dimethylformamide, dimethylacetamide, dimethylsulfoxide, acetonitrile, ethyl ether, tetrahydrofuran, dioxane, chloroform, water or the like.

The reaction temperature may be $-5°$ C.$-+100°$ C. or preferably $+20°$ C.$-+80°$ C. By proceeding with the reaction for 1-6 hours, the compound of this invention can be obtained with high yield and high purity.

In order to obtain the corresponding compound of the general formula (I) in its free form from the thus-obtained hydrochloride, it is necessary to treat the hydrochloride with a base, for example, an inorganic base such as sodium hydroxide, potassium hydroxide, potassium carbonate, sodium carbonate, sodium hydrogencarbonate or ammonia or an organic base such as pyridine or triethylamine. In order to derive other salts, it is required to treat the free compound with corresponding acids, for example, sulfuric acid, carbonic acid, nitric acid, hydrobromic acid, phosphoric acid, sulfonic acid, acetic acid, oxalic acid, tartaric acid, citric acid, malic acid, glutamic acid, aspartic acid and/or the like.

The compound of the formula (II), which is employed as a raw material in the above process, can be prepare, for example, in accordance with the following reaction scheme, namely, by reacting an amine (V) with a diketene (IV) to obtain a compound (VI) and then chlorinating the compound (VI) with sulfuryl chloride [Chemical Abstracts, 19, 43 (1925)], N-chlorosuccinimide or the like.

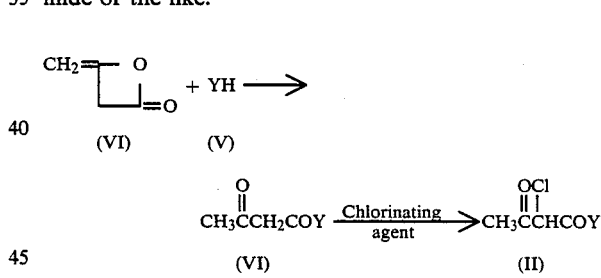

wherein Y has the same meaning as defined above.

The other raw material (III) can be prepared, for example, in the following manner base on the process described in Org. Synth. Coll. 3, 394:

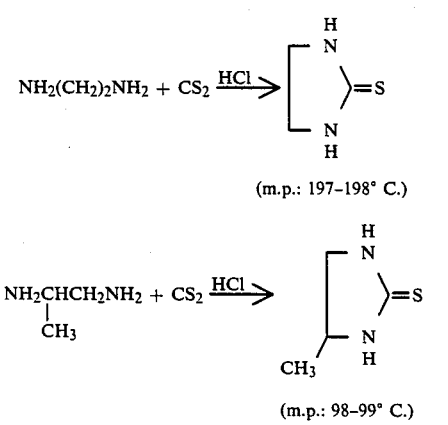

-continued

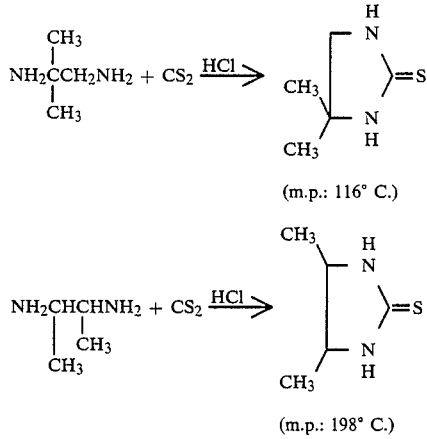

(m.p.: 116° C.)

(m.p.: 198° C.)

When the group represented by Y is

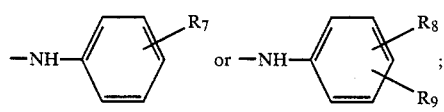

in the compounds (I) of this invention obtained in the above manner, the following specific groups may be mentioned as preferred examples of these groups:

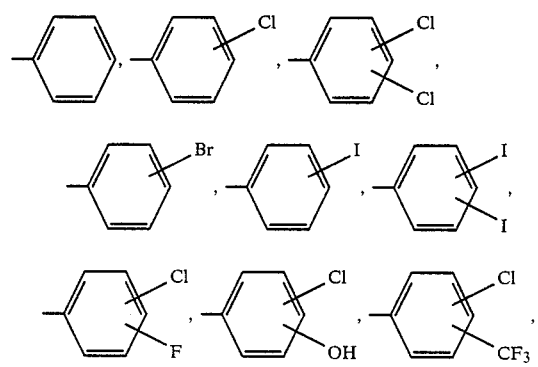

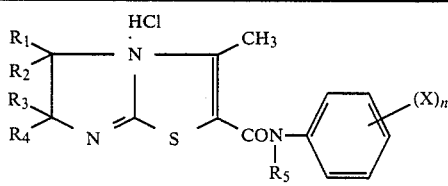

When Y stands for any one of the above exemplified groups, at least one of $R_1$, $R_2$, $R_3$ and $R_4$ means a methyl group. The methyl group is substituted to the 5- or 6-position of the imidazothiazole skeleton. The 6-substituted compound is preferred.

[Effects]

Pharmacological effects of the compounds (I) of this invention and their salts will next be described Test 1

Effect on anti-SRBC PFC response in vitro:

In an RPMI-1640 culture medium containing 10% of fetal calf serum (FCS), $1 \times 10^7$ spleen cells of BALB/c mouse were cultured together with sheep erythrocytes ($1 \times 10^6$) and a sample compound (0.2 or 1 μg/ml) for 5 days in a $CO_2$ incubator (37° C.) in accordance with the method reported by Mischell, R. I. et al. in J. Exp. Med. 126, 423 (1967) (with some modifications). The number of resultant plaque forming cells was counted by the method proposed by Jerne and Nordin [Science 140, 405 (1963)]. Results are shown in Table 1-A - Table 1-C.

TABLE 1-A (Ia)

| Sample compound (1 μg/ml) | $R_1$ | $R_2$ | $R_3$ | $R_4$ | $R_5$ | $X_n$ | Immune response potentiation activities (Control = 100%) |
|---|---|---|---|---|---|---|---|
| Comp'd 1 | H | H | H | H | $CH_3$ | 3,4-$Cl_2$ | 377 |
| Comp'd 30 | H | H | $CH_3$ | $CH_3$ | $CH_3$ | 3-$CF_3$ | 271 |
| Comp'd 31 | H | H | $CH_3$ | $CH_3$ | $CH_3$ | 3,4-$Cl_2$ | 201 |
| Comp'd 32 | H | H | $CH_3$ | $CH_3$ | $CH_3$ | 3,5-$(CF_3)_2$ | 199 |
| Comp'd 3 | H | H | $CH_3$ | $CH_3$ | $CH_3$ | 4-$CF_3$ | 203 |
| Comp'd 2 | H | H | $CH_3$ | $CH_3$ | $CH_3$ | 3,5-$Cl_2$ | 293 |
| Comp'd 4 | H | H | $CH_3$ | $CH_3$ | $C_2H_5$ | 3,4-$Cl_3$ | 177 |

TABLE 1-B

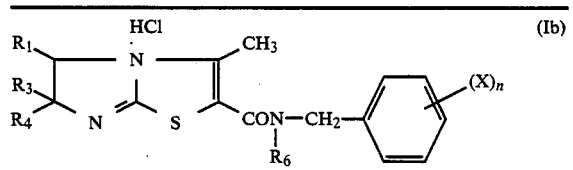
(Ib)

| Sample compound | R₁ | R₃ | R₄ | R₆ | Xₙ | Immune response potentiation activities (Control = 100%) 0.2 µg/ml | 1 µg/ml |
| --- | --- | --- | --- | --- | --- | --- | --- |
| Comp'd 45 | H | H | H | H | 4-Cl | 252 | 302 |
| Comp'd 55 | H | H | H | H | 2,4-Cl₂ | 183 | — |
| Comp'd 56 | H | H | H | H | 3,4-Cl₂ | 239 | — |
| Comp'd 60 | H | H | H | H | 3,5-Cl₂ | — | 190 |
| Comp'd 51 | H | H | H | CH₃ | 2,4-Cl₂ | — | 267 |
| Comp'd 48 | H | H | H | CH₃ | 3,4-Cl₂ | 341 | — |
| Comp'd 66 | H | H | H | CH₃ | 3-Cl | 173 | — |
| Comp'd 88 | H | CH₃ | CH₃ | H | 3-Cl | — | 212 |
| Comp'd 89 | H | CH₃ | CH₃ | H | 4-Cl | — | 168 |
| Comp'd 91 | H | CH₃ | CH₃ | H | 3,4-Cl₂ | 220 | — |
| Comp'd 92 | H | CH₃ | CH₃ | H | 3-CF₃ | 361 | 638 |
| Comp'd 94 | H | CH₃ | CH₃ | CH₃ | 3-Cl | — | 181 |
| Comp'd 95 | H | CH₃ | CH₃ | CH₃ | 3-CF₃ | 186 | — |
| Comp'd 96 | H | CH₃ | CH₃ | CH₃ | 3,4-Cl₂ | 186 | — |
| Comp'd 44 | H | CH₃ | CH₃ | CH₃ | 4-Cl | — | 149 |
| Comp'd 49 | CH₃ | CH₃ | H | H | 3,4-Cl₂ | 193 | — |
| Comp'd 85 | CH₃ | CH₃ | H | H | 3-CF₃ | — | 193 |
| Comp'd 87 | CH₃ | CH₃ | H | CH₃ | 3-Cl | 179 | — |

Note: "—" means that no measurement was conducted. ("—" will have the same meaning in the subsequent Tables.)

TABLE 1-C

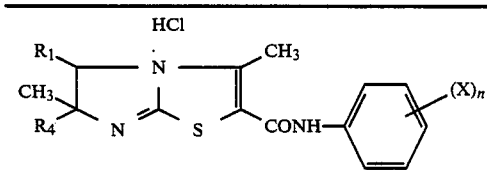
(Ic)

| Sample compound | R₁ | R₄ | Xₙ | Immune response potentiation activities (Control = 100%) 0.2 µg/ml | 1 µg/ml |
| --- | --- | --- | --- | --- | --- |
| Comp'd 141 | H | H | 3-Cl | 750 | 842 |
| Comp'd 137 | H | H | 3,4-I₂ | 316 | 561 |
| Comp'd 142 | H | H | 4-Cl | — | 471 |
| Comp'd 140 | H | H | 2-Cl | — | 198 |
| Comp'd 144 | H | H | 3,4-Cl₂ | 405 | 663 |
| Comp'd 145 | H | H | 3,5-Cl₂ | 318 | 382 |
| Comp'd 155 | H | H | 2-Cl, 4-CF₃ | 208 | 439 |
| Comp'd 160 | H | CH₃ | 3,4-Cl₂ | — | 896 |
| Comp'd 135 | H | CH₃ | 4-Cl | — | 230 |
| Comp'd 134 | H | CH₃ | 3-Cl | 520 | — |
| Comp'd 166 | H | CH₃ | 3,5-(CF₃)₂ | 339 | 420 |
| Comp'd 136 | H | CH₃ | 3-Cl, 4-CF₃ | 527 | — |
| Comp'd 167 | H | CH₃ | H | — | 267 |
| Comp'd 138 | CH₃ | H | 3,4-Cl₂ | 261 | 839 |
| Comp'd 157 | CH₃ | H | 3,4-I₂ | 239 | 266 |

For the sake of comparison, effects on in-vitro plaque forming cell response were also measured in the same manner with respect to the following compounds which are described in Japanese Patent Laid-Open No. 106893/1977 and J. Med. Chem., 24, 604–609 (1981). Results are shown in Table 1-D.

TABLE 1-D

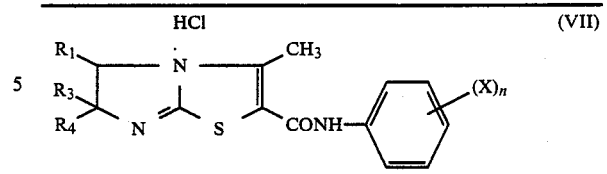
(VII)

| Sample compound | R₁ | R₃ | R₄ | Xₙ | Immune response potentiation activities (Control = 100%) 0.2 µg/ml | 1 µg/ml |
| --- | --- | --- | --- | --- | --- | --- |
| Comparative Compound 1 | H | H | H | 2-F | 78 | — |
| Comparative Compound 2 | H | H | H | 2,6-Cl₂ | 82 | 126 |
| Comparative Compound 3 | H | H | H | 2,4,6-(CH₃)₃ | — | 127 |
| Comparative Compound 4 | H | CH₃ | CH₃ | 2,4,6-(CH₃)₃ | 121 | 132 |
| Comparative Compound 5 | H | CH₃ | H | 2,4,6-(CH₃)₃ | 100 | 119 |

As apparent from Table 1-A–Table 1-D, the compounds of this invention showed activities higher than levamisole at a low concentration of 0.2 or 1 µg/ml in the above test in which levamisole required a concentration as high as about 20 µg/ml to exhibit potentiation activities. On the other hand, the comparative compounds exhibited substantially no activities.

Test 2

Effect on lymphocyte blstoenic response in vitro:

In an RPMI-1640 culture medium (0.2 ml) containing 5% of fetal calf serum (FCS) BALB/C mo spleen cells ($1 \times 10^5$) or thymus cells ($2 \times 10^5$) were cultured together with mitogen (Con A: 2.5 µg/ml; or LPS: 10 µg/ml) and a sample compound(1 µg/ml) for 48 hours in a $CO_2$ incubator (37° C.). Then, 0.5 µCi of $^3$H-thymidine was added, followed by further cultivation for 18 hours. The radioactivity of $^3$H-thymidine taken in the cells was thereafter measured Results are summarized in Table 2.

TABLE 2

| Sample compound (1 µg/ml) | Incorporation ratio of $^3$H-thymidine (Control = 100%) | | |
| --- | --- | --- | --- |
| | Spleen cells | | Thymus cells |
| | Con A stimulation | LPS stimulation | Con A stimulation |
| Compound 141 | 131 | 169 | — |
| Compound 142 | 166 | 234 | 215 |
| Compound 144 | 148 | 197 | 157 |
| Compound 135 | 182 | 263 | — |
| Compound 145 | 133 | 174 | — |
| Compound 134 | 136 | 233 | 164 |
| Compound 48 | 136 | — | 148 |
| Compound 91 | 151 | — | — |
| Compound 163 | 140 | 174 | 122 |

The compounds of this invention apparently stimulated the incorporation of $^3$H-thymidine.

Test 3

Effect on lymphocyte blastogenic response in vivo:

A group of six BALB/C mice were used. A sample compound was orally administered at a daily dose of 0.25 mg/Kg, once a day, for 5 days. On the sixth day spleens were taken out. Spleen cells ($2 \times 10^5$) were cultured together with mitogen (Con A: 2.5 μg/ml; or LPS 10 μg/ml) to investigate the lymphocyte blastogenic response. Culturing conditions were the same as those employed in Test 2 and the measurement of the lymphocyte blastogenic response was effected in accordance with the method used in Test 2. Although levamisole required its administration at a dose of 2.5 mg/Kg/day to show its effects in the present test, the compounds of this invention showed promoting activities equal to or higher than levamisole at a dose one tenth of levamisole, i.e., at a dose of 0.25 mg/Kg/day (Table 3).

TABLE 3

| Sample compound | Incorporation ratio of $^3$H-thymidine (Control: 100%) | |
|---|---|---|
| | Con A stimulation | LPS stimulation |
| Compound 136 | 240 ± 18 | 210 ± 9 |
| Compound 167 | 155 ± 10 | 111 ± 9 |
| Compound 134 | 310 ± 22 | 125 ± 9 |
| Compound 51 | 142 ± 26 | 118 ± 12 |
| Compound 49 | 195 ± 8 | 156 ± 4 |
| Compound 91 | 256 ± 17 | 176 ± 16 |
| Compound 44 | 155 ± 19 | 115 ± 6 |

Test 4

Effect on delayed-type allergic response:

A group of eight ddY mice were sensitized by injecting $2 \times 10^8$ sheep erythrocytes subcutaneously in the back of each of the mice. On the fourth day after their sensitization, $5 \times 10^7$ sheep erythrocytes were injected under the heel skin of one of the hind legs of each of the mice whereas a physiological saline was injected in the heel skin of the other hind leg. 24 hours later, the thickness of each paw was measured by a micrometer to determine the degree of swelling. Each sample compound was orally administered for 5 days, once a day, after passage of 2 hours from the sensitization. Results are shown in Table 4-A and 4-B. The compounds of this invention inhibited the delayed-type allergic response significantly by its oral administration at a dose of 0.1 mg/Kg/day.

TABLE 4-A

| Sample Compound | Dose (mg/Kg/day,po) | Degree of swelling (%) (average value ± standard deviation) |
|---|---|---|
| Control | — | 29.0 ± 9.0 |
| Compound 134 | 0.1 | 15.6 ± 4.0* |
| Compound 134 | 0.2 | 14.7 ± 4.82* |

*Significant at a level of P <0.05 against Control.

TABLE 4-B

| Sample Compound | Dose (mg/Kg/day,po) | Degree of swelling (%) (average value ± standard deviation) |
|---|---|---|
| Control | — | 24.2 ± 6.9 |
| Compound 44 | 0.1 | 17.1 ± 4.6* |

*Significant at a level of P <0.05 against Control.

Test 5

Effect on adjuvant arthritis:

(1) A group of eight Lewis male rats were employed. A suspension of 0.6 mg/0.1 ml of dead cells of Micobacterium tuberculosis in liquid paraffin was injected as an adjuvant in the heel skin of one of the hind legs of each of the rats, thereby inducing adjuvant arthritis. Besides, each sample compound was orally administered once a day for 20 days. On the 21$^{st}$ day, the paw volumes of both hind legs of each of the rats were measured to determine the degree of swelling. Results are shown in Table 5-A.

(2) A suspension of 0.6 mg/0.1 ml of dead cells of Micobacterium tuberculosis in liquid paraffin was injected as an adjuvant in the heel skin of one of the hind legs of each of eight Sprague-Dawley male rats in a group, thereby inducing adjuvant arthritis. From the 21$^{st}$ day after the injection of the adjuvant, each sample compound of this invention was orally administered everyday once a day. The volume of the paw of each hind leg, which was not injected with the adjuvant, was measured on the 7$^{th}$ and 10$^{th}$ days so that the degrees of swelling were determined. Results are shown in Table 5-B.

The compounds of this invention inhibited the swelling of the adjuvant non-injected legs and adjuvant-injected legs significantly when administered at a dose of 1 or 5 mg/Kg/day.

TABLE 5-A

| Sample compound | Dose (mg/Kg/day,po) | Degree of swelling (%) (average value ± standard deviation) | |
|---|---|---|---|
| | | Adjuvant non-injected leg | Adjuvant injected leg |
| Control | — | 173.1 ± 25.5 | 309.9 ± 27.1 |
| Comp'd 44 | 1 | 142.6 ± 29.0* | 285.9 ± 44.9 |
| Comp'd 44 | 5 | 135.1 ± 27.3* | 274.1 ± 35.4* |

*Significant at a level of P <0.05 against Control.

TABLE 5-B

| Sample compound | Dose (mg/Kg/day,po) | Degree of swelling (%) (average value ± standard deviation) | |
|---|---|---|---|
| | | 7$^{th}$ day | 10$^{th}$ day |
| Control | — | 100.5 ± 31.1 | 89.9 ± 28.5 |
| Comp'd 134 | 5 | 66.0 ± 32.8* | 59.0 ± 27.1* |

*Significant at a level of P <0.05 against Control.

Test 6:

Side effects and blood levels:

To each of four Wistar male rats in a group, each sample compound was orally administered at a dose of 300 mg/Kg, once a day, for 4 days to observe changes in general behaviors and at the same time, to investigate influence on body weight, liver weight and serum cholesterol level. The serum cholesterol level was measured by a Centriphichem Autoanalyzer, using a cholesterol measurement kit marketed by Baker, Inc. Compound 44 and 134 and for certain tests, Compound 2, 3, 30, 31 and 32, were all employed as compounds of this invention, while a compound represented by the general formula (X), in which $R_1=R_3=R_4=H$ and $(X)_n=3,4-Cl_2$ (Comparative Compound 6), and a compound represented also by the general formula (X), in which $R_1=R_3=R_4=H$ and $(X)_n=3,4-CF_3$ (Comparative Compound 7), were both used as comparative compounds. In certain tests, levamisole was also used as a comparative compound. The blood levels of the individual sample compounds were also compared after their single administration and after their administration for four days. Their blood levels were measured by means of a high-performance liquid chromatography.

(1) Effect on the general behaviors:

Although no changes were observed on the general behaviors in the groups administered respectively with the compounds of this invention and Comparative Compound 6, dacryorrhea, dacryohemorrhea, sedation, ataxia and tremor were observed in the group administered with Comparative Compound 7. In the group administered with levamisole, one half of the animals resulted in death.

(2) Effect on the body weight:

Body weights both before administration of the sample compounds and after their continuous administration for 4 days are shown in Table 6-A–Table 6-C.

TABLE 6-A

Body weight, (g)

| Sample compound | Dose (mg/Kg/day,po) | Before administration | After administration for 4 days |
|---|---|---|---|
| Control | — | 79.0 ± 3.5 | 93.0 ± 3.4 |
| Comp'd 30 | 300 | 79.0 ± 2.0 | 91.0 ± 0.8 |
| Control | — | 91.3 ± 1.5 | 104.0 ± 3.7 |
| Comp'd 31 | 300 | 91.3 ± 5.5 | 102.8 ± 7.8 |
| Control | — | 113.3 ± 1.5 | 128.5 ± 3.0 |
| Comp'd 32 | 300 | 113.8 ± 1.3 | 122.0 ± 6.5 |
| Comp'd 3 | 300 | 114.0 ± 5.7 | 126.0 ± 8.8 |
| Control | — | 87.0 ± 5.1 | 102.8 ± 5.9 |
| Comp'd 2 | 300 | 87.3 ± 2.8 | 102.0 ± 1.6 |

TABLE 6-A-continued

Body weight, (g) (average value ± standard deviation)

| Sample compound | Dose (mg/Kg/day,po) | Before administration | After administration for 4 days |
|---|---|---|---|
| Comp. Comp'd 6 | 300 | 87.3 ± 2.5 | 89.5 ± 3.0* |
| Control | — | 93.3 ± 5.7 | 108.3 ± 4.9 |
| Levamisole | 100 | 93.5 ± 4.7 | 99.5 ± 2.5* |
| Control | — | 111.0 ± 5.3 | 128.5 ± 7.0 |
| Comp. Comp'd 7 | 300 | 110.0 ± 2.3 | 115.3 ± 8.2* |

*Significant at a level of P < 0.05 against Control.

TABLE 6-B

| | | Test 1 | | Test 2 | |
|---|---|---|---|---|---|
| Sample compound | Dose (mg/Kg/day,po) | Before administration | After administration | Before administration | After administration |
| Control | — | 84.5 ± 3.1 | 100.5 ± 2.5 | 87.0 ± 5.1 | 102.8 ± 5.9 |
| Comp'd 44 | 300 | 84.0 ± 1.4 | 100.0 ± 2.9 | 87.0 ± 2.2 | 102.5 ± 3.4 |
| Comp. Comp'd 6 | 300 | 84.3 ± 6.1 | 88.8 ± 6.4* | 87.3 ± 2.5 | 89.5 ± 3.0* |

Each value indicates the average body weight (g) of 4 rats in the same group ± standard deviation.
*Significant at a level of P <0.05 against Control.

TABLE 6-C

| | | Test 1 | | Test 2 | |
|---|---|---|---|---|---|
| Sample compound | Dose (mg/Kg/day,po) | Before administration | After administration | Before administration | After administration |
| Control | — | 79.3 ± 1.0 | 97.0 ± 3.5 | 81.8 ± 2.6 | 96.0 ± 2.8 |
| Comp'd 134 | 300 | 79.5 ± 1.0 | 95.8 ± 4.2 | 82.0 ± 5.9 | 92.0 ± 5.9 |
| Comp. Comp'd 6 | 300 | 79.3 ± 1.5 | 89.5 ± 3.0* | — | — |

Each value indicates the average body weight (g) of 4 rats in the same group ± standard deviation.
*Significant at a level of P <0.05 against Control.

Although neither Compound 44 nor Compound 134 gave any effects to the body weight, Comparative Compound 6 decreased the body weight significantly against Control. Levamisole decreased the body weight significantly against Control even when administered at 100 mg/Kg/day.

(3) Effect on the liver weight

Results are shown in Table 7-A and Table 7-B. Although Compound 1 did not give any significant effect on the liver weight compared with Control, Comparative Compound 6 increased the liver weight significantly against Control.

TABLE 7-A

| | | Test 1 | | Test 2 | |
|---|---|---|---|---|---|
| Sample compound | Dose (mg/Kg/day,po) | Liver weight (g/100 g B.W.**) | Increase (%) | Liver weight (g/100 g B.W.) | Increase (%) |
| Control | — | 4.22 ± 0.03 | — | 4.13 ± 0.20 | — |
| Comp'd 44 | 300 | 4.33 ± 0.07 | 2.6 | 4.74 ± 0.65 | 14.8 |
| Comp. Comp'd 6 | 300 | 5.35 ± 0.43* | 26.8 | 5.71 ± 0.27* | 38.3 |

Each liver weight indicates the average value of 4 rats in the same group ± standard deviation.
*Significant at a level of P <0.05 against Control.
**B.W. stands for "body weight".

TABLE 7-B

| | | Test 1 | | Test 2 | |
|---|---|---|---|---|---|
| Sample compound | Dose (mg/Kg/day,po) | Liver weight (g/100 g B.W.**) | Increase (%) | Liver weight (g/100 g B.W.) | Increase (%) |
| Control | — | 4.30 ± 0.06 | — | 4.10 ± 0.22 | — |
| Comp'd 134 | 300 | 4.43 ± 0.21 | 3.0 | 4.13 ± 0.14 | 0.7 |
| Comp. | 300 | 5.62 ± 0.17* | 30.7 | 5.50 ± 0.44* | 34.1 |

TABLE 7-B-continued

| Sample compound | Dose (mg/Kg/day,po) | Test 1 Liver weight (g/100 g B.W.**) | Increase (%) | Test 2 Liver weight (g/100 g B.W.) | Increase (%) |
|---|---|---|---|---|---|
| Comp'd 6 | | | | | |

Each liver weight indicates the average value of 4 rats in the same group ± standard deviation.
*Significant at a level of P <0.05 against Control.
**B.W. stands for "body weight".

(4) Effect on the serum cholesterol level:

Test results are shown in Table 8-A and Table 8-B. Neither Compound 44 nor Compound 134 gave any significant effects to the serum cholesterol level compared with Control, Comparative Compound 6 and 7 and Levamisole increased the cholesterol level significantly against Control.

TABLE 8-A

| Sample compound | Dose (mg/Kg/day,po) | Test 1 Cholesterol (mg/dl) | Increase (%) | Test 2 Cholesterol (mg/dl) | Increase (%) |
|---|---|---|---|---|---|
| Control | — | 83.4 ± 7.8 | — | 75.2 ± 6.7 | — |
| Comp'd 44 | 300 | 81.3 ± 8.4 | −2.5 | 82.6 ± 7.1 | 9.8 |
| Comp. Comp'd 6 | 300 | 168.3 ± 16.1* | 101.8 | 157.1 ± 21.0* | 108.9 |
| Control | — | 63.0 ± 6.6 | — | 63.0 ± 3.5 | — |
| Comp. Comp'd 7 | 300 | 83.2 ± 6.2* | 32.1 | 83.9 ± 5.3* | 33.2 |
| Control | — | 73.4 ± 7.5 | — | | |
| Levamisole | 100 | 89.0 ± 4.9* | 21.3 | | |

Each liver weight indicates the average value of 4 rats in the same group ± standard deviation.
*Significant at a level of P <0.05 against Control.

TABLE 8-B

| Sample compound | Dose (mg/Kg/day,po) | Test 1 Cholesterol (mg/dl) | Increase (%) | Test 2 Cholesterol (mg/dl) | Increase (%) |
|---|---|---|---|---|---|
| Control | — | 70.6 ± 7.1 | — | 66.2 ± 2.9 | — |
| Comp'd 134 | 300 | 78.5 ± 5.8 | 11.2 | 72.9 ± 6.9 | 10.1 |
| Comp. Comp'd 6 | 300 | 134.5 ± 8.3* | 90.5 | 138.2 ± 17.0* | 108.8 |

Each cholesterol level indicates the average value of 4 rats in the same group ± standard deviation.
*Significant at a level of P <0.05 against Control.

(5) Change in blood level by repeated administration:

Table 9 shows blood levels on the $1^{st}$ and $2^{nd}$ hours after each of a single administration and an administration for 4 days, once a day. Although the blood levels of Compounds 44 and 129 were found to be close to their blood levels after their single administration even after the administration for 4 days, the blood levels of Comparative Compounds 6 and 7 dropped remarkably by their repeated administration.

TABLE 9

| Sample compound | Dose (mg/Kg/day,po) | Blood level (μg/ml) Single administration 1 hour later | 2 hours later | Administration for 4 days 1 hour later | 2 hours later |
|---|---|---|---|---|---|
| Comp'd 44 | 300 | — | 12.98 ± 3.81 | — | 10.48 ± 1.34 |
| Comp'd 134 | 300 | 4.48 ± 2.32 | 12.15 ± 2.18 | 9.75 ± 4.86 | 7.70 ± 0.79 |
| Comp. Comp'd 6 | 300 | 8.27 ± 2.40 | 4.61 ± 0.74 | 0.38 ± 0.33 | 0.16 ± 0.24 |
| Comp. Comp'd 7 | 300 | 8.48 ± 1.91 | 10.80 ± 3.53 | 3.03 ± 2.08 | 2.73 ± 1.14 |

Each blood level indicates the average value of 4 rats in the same group ± standard deviation.

The compounds of this invention may be administered, as they are or in various dosage forms, orally or parenterally (for example, by their intramuscular, subcutaneous, intravenous, rectal or cutaneous administration). As their dosable preparation forms, they may be formed into solid preparations such as tablets, sugar-coated tablets, film-coated tablets, hard and soft capsules, troches, pills, granules and powders; semi-solid preparations such as suppositories, plasters and ointments; and liquid preparations such as injectable solutions, syrups, inhalants, emulsions and suspensions. Although the compounds of this invention may be formed into the above-described preparations without any additional pharmaceutically-effective ingredients, one or more other pharmaceutically-effective ingredients such as nonsteroid analgesic and artiphlogistic agents may also be incorporated in combination.

[EXAMPLES]

The present invention will hereinafter be described further by the following Referential Examples and Examples.

Referential Example 1:

Dissolved in toluene were 3.5 g (0.02 mole) of 3,4-dichloro-N-methylaniline and a catalytic amount of pyridine, followed by a dropwise addition of 1.9 g (0.022 mole) of diketene at 50° C. After completion of the the dropwise addition, the resultant mixture was heated under reflux for 3 hours. The reaction mixture was cooled, and its organic layer was then washed with water, water, a 10% aqueous solution of hydrochloric acid and a 5% aqueous solution of sodium hydrogencarbonate in order. The thus-washed organic solution was dried nd concentrated to obtain 3',4'-dichloro-N-methylacetoacetoanilide.

Example 1:

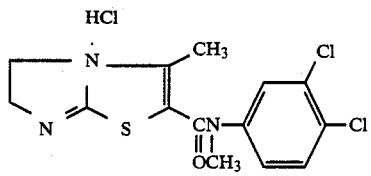

(i) Suspended in carbon tetrachloride were 2.6 g (0.01 mole) of the 3',4'-dichloro-N-methylacetoacetoanilide obtained in Referential Example 1 and 1.4 g (0.01 mole) of N-chlorosuccinimide, followed by an addition of a small amount of benzoyl peroxide. The resultant mixture was heated under reflux for 1 hour. The reaction mixture was then washed with water, dried and concentrated. The residue was dissolved in methyl ethyl ketone, followed by an addition of 1.0 g (0.01 mole) of imidazolidine-2-thione. The mixture was then heated under reflux for 3 hours. Precipitated crystals were collected by filtration, recrystallized from ethanol and then dried under reduced pressure, thereby obtaining 3.4 g of 3',4'-dichloro-N,3-dimethyl-5,6-dihydroimidazo[2,1-b]thiazole-2-carboxyanilide hydrochloride (Compound 1) [yield: 89.5%]. Melting point: 275°-276° C.

(ii) Dissolved in water was 1.9 g (0.005 mole) of the thus-obtained hydrochloride, followed by a dropwise addition with stirring of a 10% aqueous solution of caustic soda at room temperature. Resultant crystals were collected by filtration and washed with a great deal of water to purify same. The thus-washed crystals were dried under reduced pressure to obtain 1.4 g of 3',4'-dichloro-N,3-dimethyl-5,6-dihydroimidazo[2,1-b]-thiazole-2-carboxyanilide (yield: 82.4%). Melting point: 118°-122° C.

Example 2:

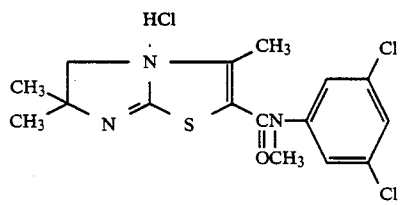

(i) Suspended in carbon tetrachloride were 1.4 g (0.01 mole) of 3',5'-dichloro-N-methylacetoacetoanilide, obtained in the same manner as in Referential Example 1, and 1.4 g (0.01 mole) of N-chlorosuccinimide, followed by an addition of a small amount of benzoyl peroxide. The resultant mixture was heated under reflux for 1 hour. The reaction mixture was washed with water, dried and then concentrated. The residue was dissolved in methyl ethyl ketone, followed by an addition of 1.3 g (0.01 mole) of 4,4-dimethylimidazolidine-2-thione. The resultant mixture was heated under reflux for 3 hours. Precipitated crystals were collected by filtration, recrystallized from isopropanol and then dried under reduced pressure, thereby obtaining 3.0 g of 3',5'-dichloro-N,3,6,6-tetramethyl-5,6-dihydroimidazo[2,1-b]thiazole-2-carboxyanilide hydrochloride (Compound 2) [yield: 75.0%]. Melting point: 222°-230° C.

(ii) Dissolved in water was 2.0 g (0.005 mole) of the above-obtained hydrochloride, followed by a dropwise addition with stirring of a 20% aqueous solution of potassium carbonate at room temperature. Resultant crystals were collected by filtration and then washed with a great deal of water for its purification. The thus-purified crystals were dried under reduced pressure to obtain 1.5 g of 3',5'-dichloro-N,3,6,6-tramethyl-5,6-dihydroimidazo[2,1-b]thiazole-2-carboxyanilide (yield: 78.9%).

Melting point: 169° C.

Example 3:

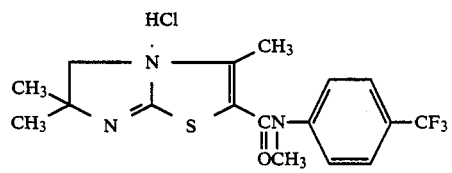

Dissolved in diethyl ether was 2.6 g (0.01 mole) of N-methyl-4'-trifluoromethylacetoacetoanilide obtained in the same manner as in Referential Example 1, followed by a dropwise addition of 1.5 g (0.011 mole) of sulfuryl chloride at −5° C. The resultant mixture was stirred at −10°−−5° C. for 30 minutes. The reaction mixture was then poured into ice water, neutralized with sodium hydrogencarbonate and extracted with toluene. The organic layer was dried an concentrated. The residue was dissolved in methyl ethyl ketone, to which 1.3 g (0.01 mole) of 4,4-dimethylimidazolidine-2-thione was added. The mixture was heated under reflux for 3 hours. Precipitate crystals were collected by filtration, washed with acetone and then dried under reduced pressure, thereby obtaining 3.7 g of N,3,6,6-tetramethyl-4'-trifluoromethyl-5,6-dihydroimidazo- [2,1-b]-thiazole-2-carboxyanilide hydrochloride (Compound 3) [yield: 92.5%]

Melting point: 195°-198° C.

Example 4:

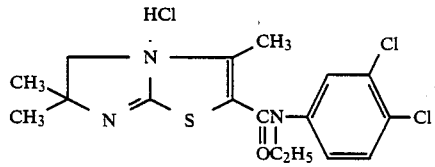

Suspended in carbon tetrachloride were 2.7 g (0.01 mole) of 3',4'-dichloro-N-ethylacetoacetoanilide, obtained in the same manner as in Referential Example 1, and 1.4 g (0.01 mole) of N-chlorosuccinimide, followed by an addition of a small amount of benzoyl peroxide. The resultant mixture was heated under reflux for 1 hour. The reaction mixture was washed with water, dried and then concentrated. The residue was dissolved in methyl ethyl ketone, followed by an addition of 1.3 g (0.01 mole of 4,4-dimethylimidazolidine-2-thione. The resultant mixture was heated under reflux for 3 hours. Precipitated crystals were collected by filtration, washed with acetone and then dried under reduced pressure, thereby obtaining 3.3 g of 3',4'-dichloro-N-ethyl-3,6,6-trimethyl-5,6-dihydroimidazo[2,1-b]thiazole-2-carboxyanilide hydrochloride (Compound 4) [yield: 78.6%].

Melting point: 210°-214° C.

Example 5:

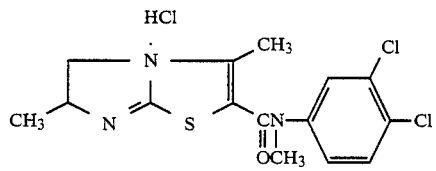

Following the procedure of Example 2, 2.6 g (0.01 mole) of 3',4'-dichloro-N-methylacetoacetanilide obtained in Referential Example 1 was chlorinated. The resultant oily substance was dissolved in methyl ethyl ketone, followed by an addition of 1.2 g (0.01 mole) of 4-methylimidazolidine-2-thione. The resulting mixture was heated under reflux for 3 hours. Precipitated crystals were collected by filtration, followed by its washing with acetone to obtain 3.6 g of 3',4'-dichloro-N,3,6-trimethyl-5,6-dihydroimidazo[2,1-b]thiazole-2-carboxyanilide hydrochloride (Compound 5) [yield: 92.3%].

Melting point: 230°-231° C.

Example 6:

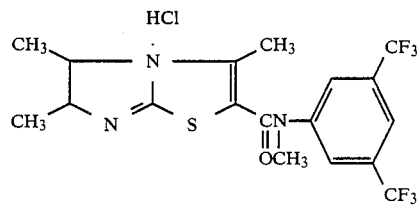

Suspended in carbon tetrachloride were 3.2 g (0.01 mole) of N-methyl-3',5'-bis(trifluoromethyl)acetoacetoanilide, obtained in the same manner as in Referential Example 1, and 1.4 g (0.01 mole) of N-chlorosuccinimide, followed by an addition of a small amount of benzoyl peroxide. The resultant mixture was heated under reflux for 1 hour. The reaction mixture was washed with water, dried and then concentrated. The residue was dissolved in methyl ethyl ketone, followed by an addition of 1.3 g (0.01 mole) of 4,4-dimethylimidazolidine-2-thione. The resultant mixture was heated under reflux for 3 hours. Precipitated crystals were collected by filtration, washed with acetone and then dried under reduced pressure, thereby obtaining 3.5 g of N,3,5,6-tetramethyl-3',5'-bis(trifluoromethyl)-5,6-dihydroimidazo[2,1-b]thiazole-2-carboxyanilide hydrochloride (Compound 6) [yield: 74.5%].

Melting point: 214°-218° C.

Examples 7–43:

The following compounds were prepared in the same manner as in Referential Example 1 and Examples 1 –6.

| No. | R$_1$ | R$_2$ | R$_3$ | R$_4$ | R$_5$ | X$_n$ | Appearance | Melting point (°C.) |
|---|---|---|---|---|---|---|---|---|
| 7 | H | H | H | H | CH$_3$ | 3,4-(OCH$_3$)$_2$ | Light brownish crystals | 249–253 |
| 8 | H | H | H | H | CH$_3$ | 4-OC$_2$H$_5$ | White powder | 205–209 |
| 9 | H | H | H | H | CH$_3$ | 3,5-(OCH$_3$)$_2$ | Light Brownish powder | 222–224 |
| 10 | H | H | H | H | CH$_3$ | H | Light brownish crystals | 240–242 |
| 11 | H | H | H | H | CH$_3$ | 4-Cl | Slightly yellowish platy crystals | 257–260 |
| 12 | H | H | H | H | CH$_3$ | 3-OC$_3$H$_7$-i | White powder | 209–210 |
| 13 | H | H | H | H | CH$_3$ | 3-CF$_3$ | White powder | 228–235 |
| 14 | H | H | H | H | CH$_3$ | 2-CH$_3$, 4-Cl | Yellowish granular crystals | 267–270 |
| 15 | H | H | H | H | CH$_3$ | 2-Cl, 4-CF$_3$ | Brown powder | 184–192 |
| 16 | H | H | H | H | CH$_3$ | 3-Cl | Light yellow powder | 210–215 |
| 17 | H | H | H | H | CH$_3$ | 3,5-(CF$_3$)$_2$ | Light yellow powder | 274–276 |
| 18 | H | H | H | H | CH$_3$ | 4-CF$_3$ | Yellow powder | 235–239 |
| 19 | H | H | H | H | C$_2$H$_5$ | 3,4-Cl$_2$ | Light brownish crystals | 255–258 |
| 20 | H | H | H | H | C$_2$H$_5$ | 3-CF$_3$ | Light brownish crystals | 232–234 |
| 21 | H | H | H | H | C$_2$H$_5$ | 2-Cl, 4-CF$_3$ | Brown crystals | 220–229 |
| 22 | H | H | H | H | C$_3$H$_7$ | 3,4-Cl$_2$ | Milky white crystals | 250–254 |
| 23 | H | H | H | H | C$_3$H$_7$-i | 3-OC$_3$H$_7$-i | White powder | 187–189 |
| 24 | H | H | H | H | C$_3$H$_7$-i | 3,4-Cl$_2$ | Milky white crystals | 250–254 |
| 25 | H | H | H | H | C$_3$H$_7$-i | 4-Cl | White crystals | 228–231 |
| 26 | H | H | H | H | C$_3$H$_7$-i | 3-CF$_3$ | Light brownish crystals | 197–198 |
| 27 | H | H | H | H | C$_3$H$_7$-i | 3,5-Cl$_2$ | White powder | 250–254 |
| 28 | CH$_3$ | H | CH$_3$ | H | CH$_3$ | 4-F | Milky white powder | 195–198 |
| 29 | H | H | CH$_3$ | H | CH$_3$ | 3-Cl | Dark yellow powder | unmeasurable |
| 30 | H | H | CH$_3$ | CH$_3$ | CH$_3$ | 3-CF$_3$ | Milky white powder | 202–210 |
| 31 | H | H | CH$_3$ | CH$_3$ | CH$_3$ | 3,4-Cl$_2$ | Light brownish crystals | 202–206 |
| 32 | H | H | CH$_3$ | CH$_3$ | CH$_3$ | 3,5-(CF$_3$)$_2$ | Yellowish brown powder | 168–170 |
| 33 | H | H | CH$_3$ | CH$_3$ | CH$_3$ | 2-Cl, 4-CF$_3$ | Light brownish crystals | 222–224 |
| 34 | H | H | CH$_3$ | CH$_3$ | C$_2$H$_5$ | 2-Cl, 4-CF$_3$ | Light brownish platy crystals | 230–235 |
| 35 | H | H | CH$_3$ | CH$_3$ | C$_2$H$_5$ | 3-CF$_3$ | Yellow crystals | 51–52 |
| 36 | H | H | CH$_3$ | CH$_3$ | C$_3$H$_7$ | 3,4-Cl$_2$ | White crystals | 214–218 |
| 37 | H | H | CH$_3$ | CH$_3$ | C$_3$H$_7$-i | 3,4-Cl$_2$ | Milky white crystals | 220–225 |
| 38 | H | H | CH$_3$ | CH$_3$ | C$_3$H$_7$-i | 4-Cl | White crystals | 245–250 |
| 39 | H | H | CH$_3$ | CH$_3$ | C$_3$H$_7$-i | 3-CF$_3$ | Light yellowish crystals | unmeasurable |
| 40 | H | H | CH$_3$ | CH$_3$ | CH$_3$ | 4-NO$_2$ | Light yellowish crystals | 177–182 |
| 41 | H | H | CH$_3$ | CH$_3$ | CH$_3$ | 4-F | Milky white powder | 184–186 |
| 42 | H | H | CH$_3$ | CH$_3$ | CH$_3$ | 3,5-Cl$_2$,4-C$_5$H$_{11}$O | Brown powder | 209–212 |

-continued

| No. | R₁ | R₂ | R₃ | R₄ | R₅ | $X_n$ | Appearance | Melting point (°C.) |
|---|---|---|---|---|---|---|---|---|
| 43 | H | H | CH₃ | CH₃ | CH₃ | 2,3,4,5,6-F₅ | Light yellowish powder | 216–222 |

Referential Example 2:

Dissolved in toluene was 3.1 g (0.02 mole) of 4-chloro-N-methyl-benzylamine, followed by an addition of a catalytic amount of pyridine and a further dropwise addition of 1.8 g (0.022 mole) of diketene at room temperature. After stirring the reaction mixture at room temperature for 3 hours, it was poured in water and then extracted with toluene. Subsequent to purification, N-methyl-N-(4-chlorobenzyl)acetamide was obtained in an oily form.

Example 44:

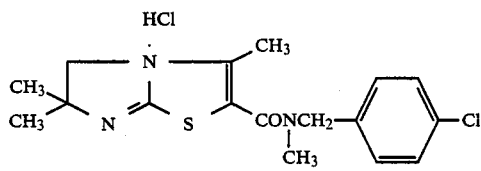

(i) Suspended in carbon tetrachloride were 4.0 g (0.017 mole) of N-methyl-N-(4-chlorobenzyl-)acetoacetamide obtained in Referential Example 2, 2.3 g (0.017 mole) of N-chlorosuccinimide and a small amount of benzoyl peroxide. The suspension was heated under reflux for 1 hour. After cooling the reaction mixture, it was poured into water and then extracted with carbon tetrachloride. The carbon tetrachloride solution was purified, dried and concentrated, thereby obtaining an oily crude product The crude product was purified on a silica gel column (c-300, n-hexane-ethyl acetate) to obtain 3.5 g of oily N-methyl-N-(4-chlorobenzyl)-2-chloroacetamide ($n_D^{20}$: 1.5336). The reaction product was then dissolved together with 1.7 g (0.013 mole) of 4,4-dimethylimidazolidine-2-thione in methyl ethyl ketone. The resultant mixture was heated under reflux for 3 hours. After cooling, the resultant precipitate was collected by filtration, washed with acetone and then recrystallized from isopropanol/isopropyl ether, thereby obtaining 4.8 g of N-(4-chlorobenzyl)-3,6,6-trimethyl-5,6-dihydroimidazo[2,1-b]thiazole-2carboxamide hydrochloride as (Compound 44)

[melting point: 187°–190° C.; white crystals].

(ii) Dissolved in water was 3.9 g (0.01 mole) of the above-obtained hydrochloride. While stirring the thus-prepared aqueous solution at room temperature, a 10% aqueous solution of caustic soda was added dropwise. Resulting crystals were collected by filtration and then washed with a great deal of water to purify same. The crystals were thereafter dried under reduced pressure to obtain 3.3 g of N-(4-chlorobenzyl)-N,3,6,6-tetramethyl-5,6-dihydroimidazo[2,1-b)-thiazole-2-carboxamide (melting point: 139° C.; light yellowish powdery crystals).

Example 45:

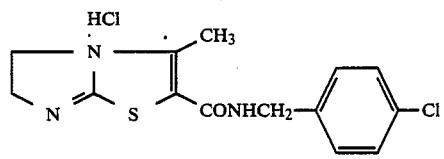

Suspended in carbon tetrachloride were 2.3 g (0.01 mole) of N-(4-chlorobenzyl)acetoacetamide obtained in the same manner as in Referential Example 2, 1.3 g (0.01 mole) of N-chlorosuccinimide an a small amount of benzoyl peroxide. The suspension was heated under reflux for 1 hour. The reaction mixture was then poured into water and extracted with carbon tetrachloride. The carbon tetrachloride solution was washed with water, dried and then concentrated. The resultant oily substance was provided for the following reaction without purifying same beforehand. Namely, the thus-obtained compound and 1.0 g (0.01 mole) of imidazolidine-2-thione were suspended in methyl ethyl ketone and the resultant suspension was heated under reflux for 3 hours. After cooling the reaction mixture, the resultant precipitate was collected by filtration, washed with acetone and then recrystallized from isopropyl alcohol-/isopropyl ether, thereby obtaining 2.8 g of N-(4-chlorobenzyl)-3-methyl-5,6-dihydroimidazo[2,1-b]thiazole-2-carboxamide hydrochloride (Compound 45).

Melting point: 241°–242° C. White crystals.

Example 46:

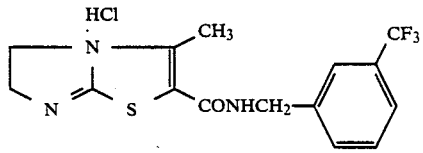

Suspended in carbon tetrachloride were 2.6 g (0.01 mole) of N-(3-trifluoromethylbenzyl)acetoacetamide obtained in the same manner as in Referential Example 2, 1.3 g (0.01 mole) of N-chlorosuccinimide and a small amount of benzoyl peroxide. The suspension was heated under reflux for 1 hour. After cooling the reaction mixture, it was poured into water and extracted with carbon tetrachloride. The carbon tetrachloride solution was washed with water, dried and then concentrated. The resultant oily substance was provided for the following reaction without purifying same beforehand. Namely, the thus-obtained compound and 1.0 g (0.01 mole) of imidazolidine-2-thione were suspended in methyl ethyl ketone and the resultant suspension was heated under reflux for 3 hours. After cooling the reaction mixture, the resultant precipitate was collected by filtration, washed with acetone and then recrystallized from ethanol, thereby obtaining 2.5 g of 3-methyl-N-(3-trifluoromethylbenzyl)-5,6-dihydroimidazo[2,1- b]thiazole-2-carboxamide hydrochloride (Compound 46)

[melting point:210°-216° C.; colorless prism-like crystals].

Example 47:

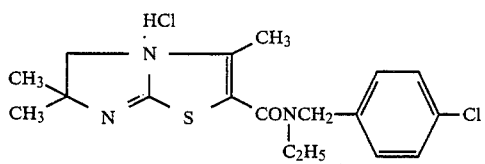

Suspended in carbon tetrachloride were 2.5 g (0.01 mole) of N-ethyl-N-(4-chlorobenzyl)acetoacetamide obtained in the same manner as in Referential Example 2, 1.3 g (0.01 mole) of N-chlorosuccinimide and a small amount of benzoyl peroxide. The suspension was heated under reflux for 1 hour. After cooling the reaction mixture, it was poured into water and extracted with carbon tetrachloride. The carbon tetrachloride solution was washed with water dried and then concentrated. The resultant oily substance was provided for the following reaction without purifying same beforehand. Namely, the thus-obtained compound and 1.3 g (0.01 mole) of 4,4-dimethylimidazolidine-2-thione were dissolved in methyl ethyl ketone and the resultant solution was heated under reflux for 3 hours. After cooling the reaction mixture, the resultant precipitate was collected by filtration, washed with acetone and then recrystallized from isopropanol/isopropyl ether, thereby obtaining 2.7 g of N-(4-chlorobenzyl)-N-ethyl-3,6,6-trimethyl-5,6-dihydroimido[2,1-b]thiazole-2-carboxamide hydrochloride (Compound 47)

[melting point: 178°-181° C.; white crystals].

Example 48:

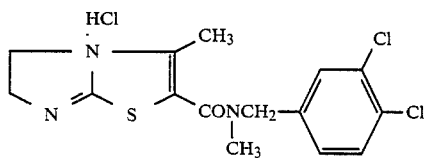

Suspended in carbon tetrachloride were 2.6 g (0.01 mole) of N-methyl-N-(3,4-dichlorobenzyl)acetoacetamide obtained in the same manner as in Referential Example 2, 1.3 g (0.01 mole) of N-chlorosuccinimide and a small amount of benzoyl peroxide. The suspension was heated under reflux for 1 hour. After cooling the reaction mixture, it was poured into water and extracted with carbon tetrachloride. The carbon tetrachloride solution was washed with water, dried and then concentrated. The resultant oily substance was provided for the following reaction without purifying same beforehand. Namely, the thus-obtained compound and 1.0 g (0.01 mole) of imidazolidine-2-thione were suspended in methyl ethyl ketone and the resultant suspension was heated under reflux for 3 hours. After cooling the reaction mixture, the resultant precipitate was collected by filtration, washed with acetone and then recrystallized from ethanol, thereby obtaining 3.1 g of N-(3,4-dichlorobenzyl)-N,3-dimethyl-5,6-dihydroimidazo[2,1-b]thiazole-2-carboxamide hydrochloride (Compound 48)

[melting point: 146°-148° C; light yellowish needle-like crystals].

Example 49:

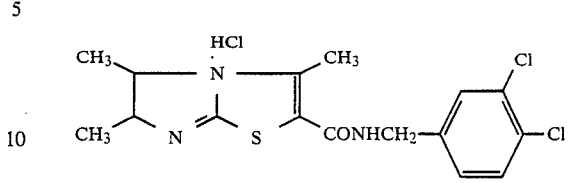

Suspended in carbon tetrachloride were 5.2 g (0.02 mole) of N-(3,4-dichlorobenzyl)acetoacetamide obtained in the same manner as in Referential Example 2, 2.7 g (0.02 mole) of N-chlorosuccinimide and a small amount of benzoyl peroxide. The suspension was heated under reflux for 1 hour. After cooling the reaction mixture, it was poured into water and extracted with carbon tetrachloride. The carbon tetrachloride solution was washed with water, dried and then concentrated. The resultant oily substance was provided for the following reaction without purifying same beforehand. Namely, the thus-obtained compound and 2.6 g (0.02 mole) of 4,5-dimethylimidazolidine-2-thione were dissolved in methyl ethyl ketone and the resultant solution was heated under reflux for 3 hours. After cooling the reaction mixture, the resultant precipitate was collected by filtration add then washed and purified with a great deal of acetone, thereby obtaining N-(3,4-dichlorobenzyl)-3,5,6-trimethyl-5,6-dihydroimidazo[2,1-b]thiazole-2-carboxamide hydrochloride (Compound 49) [melting point: 148°-152° C.; white crystals].

Example 50:

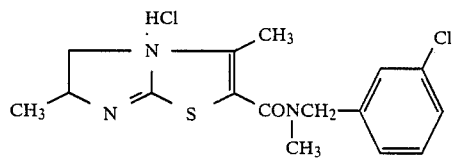

Suspended in carbon tetrachloride were 4.8 g (0.02 mole) of N-(3-chlorobenzyl)-N-methylacetamide obtained in the same manner as in Referential Example 2, 2.7 g (0.02 mole) of N-chlorosuccinimide and a small amount of benzoyl peroxide. The suspension was heated under reflux for 1 hour. It was then poured into water and extracted with carbon tetrachloride. The carbon tetrachloride solution was washed with water, dried and then concentrated. The resultant oily substance was provided for the following reaction without purifying same beforehand. Namely, the thus-obtained compound and 2.4 g (0.02 mole) of 4-methylimidazolidine-2-thione were dissolved in methyl ethyl ketone and the resultant solution was heated under reflux for 3 hours. After cooling the reaction mixture, the resultant precipitate was collected by filtration and then washed and purified with acetone and isopropyl ether, thereby obtaining N-(3-chlorobenzyl)-N,3,6-trimethyl-5,6-dihydroimidazo[2,1-b]-hiazole-2-carboxamide hydrochloride (Compound 50)

[melting point: 41°-47° C.; brownish glassy matter].

Example 51:

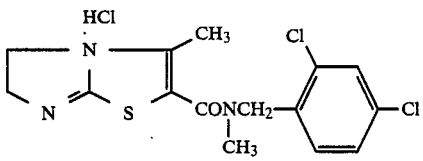

(i) Suspended in carbon tetrachloride were 5.2 g (0.02 mole) of N-(2,4-dichlorobenzyl)-N-methylacetamide obtained in the same manner as in Referential Example 2, 2.7 g (0.02 mole) of N-chlorosuccinimide and a small amount of benzoyl peroxide. The suspension was heated under reflux for 1 hour. After cooling the reaction mixture, it was poured into water and extracted with carbon tetrachloride. The carbon tetrachloride solution was washed with water, dried and then concentrated. The resultant oily substance was provided for the following reaction without purifying same beforehand. Namely, the thus-obtained compound and 1.0 g (0.01 mole) of imidazolidine-2-thione were suspended in methyl ethyl ketone and the resultant suspension was heated under reflux for 3 hours. After cooling the reaction mixture, the resultant precipitate was collected by filtration and then washed and purified with acetone, thereby obtaining 5.3 g of N-(2,4-dichlorobenzyl)-N,3-dimethyl-5,6-dihydroimidazo[2,1-b]thiazole-2-carboxamide hydrochloride (Compound 51)
[melting point: 251°–255° C.; colorless powder].

(ii) Dissolved in water was 3.6 g (0.01 mole) of the thus-obtained 2-[N-methyl-N-(2,4-dichlorobenzyl)carbmoyl]-3-methyl-5,6-dihydroimidazo[2,1-b]thiazole hydrochloride. While stirring the solution at room temperature, aqueous ammonia was added dropwise. The resultant precipitate was collected by filtration and then washed and purified with a great deal of water, thereby obtaining 3.0 g of N-(2,4-dichlorobenzyl)-N,3-dimethyl-5,6-dihydrommidazo[2,1-b]thiazole-2-carboxamide
(melting point: 55°–60° C.; light yellowish crystals).

Examples 52–133:

The following compounds were prepared in the same manner as in Referential Example 2 and Examples 44–51.

| Compound No. | $R_1$ | $R_2$ | $R_3$ | $R_4$ | $R_6$ | A | $X_n$ | Appearance | Melting point (°C.) |
|---|---|---|---|---|---|---|---|---|---|
| 52 | H | H | H | H | H | $CH_2$ | H | White prism-like crystals | 260–270 |
| 53 | H | H | H | H | H | $CH_2$ | 2-Cl | Black prism-like crystals | 242–250 |
| 54 | H | H | H | H | H | $CH_2$ | 3-Cl | White powder | 233–235 |
| 55 | H | H | H | H | H | $CH_2$ | 2,4-$Cl_2$ | Colorless crystals | 275 |
| 56 | H | H | H | H | H | $CH_2$ | 3,4-$Cl_2$ | Colorless fine needle-like crystals | 273 |
| 57 | H | H | H | H | H | $CH_2$ | 4-$CH_3$ | White powder | 233–235 |
| 58 | H | H | H | H | H | $CH_2$ | 4-$OCH_3$ | Light yellowish crystals | 192–194 |
| 59 | H | H | H | H | H | $CH_2$ | 4-$NO_2$ | White powder | 243–248 |
| 60 | H | H | H | H | H | $CH_2$ | 3,5-$Cl_2$ | Milky white crystals | 250–253 |
| 61 | H | H | H | H | $CH_3$ | $CH_2$ | H | White prism-like crystals | 187–189 |
| 62 | H | H | H | H | $CH_3$ | $CH_2$ | 2-Cl | Light yellowish powder | 189–192 |
| 63 | H | H | H | H | $CH_3$ | $CH_2$ | 4-Cl | Light yellowish prism-like crystals | 126–130 |
| 64 | H | H | H | H | $CH_3$ | $CH_2$ | 4-$CH_3$ | Light brownish crystals | 195–197 |
| 65 | H | H | H | H | $CH_3$ | $CH_2$ | 4-$OCH_3$ | White crystals | 118–119 |
| 66 | H | H | H | H | $CH_3$ | $CH_2$ | 3-Cl | Yellowish brown glassy matter | 52–58 |
| 67 | H | H | H | H | $CH_3$ | $CH_2$ | 3-$CF_3$ | Yellowish brown crystals | 31–34 |
| 68 | H | H | H | H | $CH_3$ | $CH_2$ | 3,5-$Cl_2$ | Milky white crystals | 194–195 |
| 69 | H | H | H | H | $CH_3$ | $CH_2$ | 4-F | Light brownish powder | 173–175 |
| 70 | H | H | H | H | $CH_3$ | $CH_2$ | 4-$CF_3$ | Milky white powder | 212–215 |
| 71 | H | H | H | H | $CH_3$ | $CH_2$ | 4-$OC_2H_5$ | Milky white powder | 179–180 |
| 72 | H | H | H | H | $CH_3$ | $CH_2$ | 4-$C_2H_5$ | Light brownish crystals | 195–200 |
| 73 | H | H | H | H | $CH_3$ | $CH_2$ | 4-$NO_2$ | Pinkish powder | 236–238 |
| 74 | H | H | H | H | $C_2H_5$ | $CH_2$ | 4-Cl | White crystals | 202–205 |
| 75 | H | H | H | H | $C_2H_5$ | $CH_2$ | 3,4-$Cl_2$ | Milky white crystals | 247–250 |
| 76 | H | H | H | H | $C_2H_5$ | $CH_2$ | 3-$CF_3$ | Light brownish crystals | 170–175 |
| 77 | H | H | H | H | n-$C_3H_7$ | $CH_2$ | 3,4-$Cl_2$ | Milky white crystals | 233–237 |
| 78 | H | H | H | H | i-$C_3H_7$ | $CH_2$ | 4-Cl | White crystals | 225–230 |
| 79 | H | H | H | H | i-$C_3H_7$ | $CH_2$ | 3-Cl | Light brownish crystals | 202–205 |
| 80 | H | H | H | H | i-$C_3H_7$ | $CH_2$ | 3-$CF_3$ | Yellowish crystals | 233–236 |
| 81 | H | H | H | H | i-$C_4H_9$ | $CH_2$ | 4-Cl | White crystals | 237–238 |
| 82 | H | H | $CH_3$ | H | H | $CH_2$ | 3-Cl | Milky white powder | 148–150 |
| 83 | $CH_3$ | H | $CH_3$ | H | H | $CH_2$ | 2,4-$Cl_2$ | White powder | 170–172 |
| 84 | $CH_3$ | H | $CH_3$ | H | H | $CH_2$ | 4-Cl | White powder | 166–167 |
| 85 | $CH_3$ | H | $CH_3$ | H | H | $CH_2$ | 3-$CF_3$ | Light brownish glassy matter | unmeasurable |
| 86 | $CH_3$ | H | $CH_3$ | H | H | $CH_2$ | 3-Cl | White crystals | 171–173 |
| 87 | $CH_3$ | H | $CH_3$ | H | $CH_3$ | $CH_2$ | 3-Cl | Brownish glassy matter | unmeasurable |
| 88 | H | H | $CH_3$ | $CH_3$ | H | $CH_2$ | 3-Cl | Yellowish brown powder | 80–93 |
| 89 | H | H | $CH_3$ | $CH_3$ | H | $CH_2$ | 4-Cl | Slightly brownish crystals | 70–79 |
| 90 | H | H | $CH_3$ | $CH_3$ | H | $CH_2$ | 2,4-$Cl_2$ | White crystals | 219–222 |
| 91 | H | H | $CH_3$ | $CH_3$ | H | $CH_2$ | 3,4-$Cl_2$ | Light yellowish crystals | 107–115 |

-continued

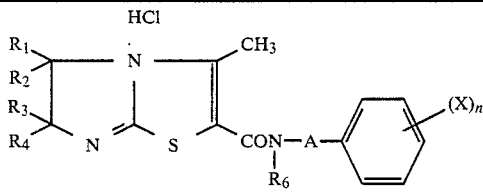

| Compound No. | R₁ | R₂ | R₃ | R₄ | R₆ | A | Xₙ | Appearance | Melting point (°C.) |
|---|---|---|---|---|---|---|---|---|---|
| 92 | H | H | CH₃ | CH₃ | H | CH₂ | 3-CF₃ | Ocher powder | 55–63 |
| 93 | H | H | CH₃ | CH₃ | H | CH₂ | 3,5-Cl₂ | Brown glassy matter | unmeasurable |
| 94 | H | H | CH₃ | CH₃ | CH₃ | CH₂ | 3-Cl | Brown glassy matter | unmeasurable |
| 95 | H | H | CH₃ | CH₃ | CH₃ | CH₂ | 3-CF₃ | Brown syrupy matter | unmeasurable |
| 96 | H | H | CH₃ | CH₃ | CH₃ | CH₂ | 3,4-Cl₂ | Light brownish glassy matter | unmeasurable |
| 97 | H | H | CH₃ | CH₃ | CH₃ | CH₂ | 3,5-Cl₂ | Yellowish crystals | unmeasurable |
| 98 | H | H | CH₃ | CH₃ | CH₃ | CH₂ | 4-F | Ocher solid matter | 155–156 |
| 99 | H | H | CH₃ | CH₃ | CH₃ | CH₂ | 4-CF₃ | Milky white powder | 218–220 |
| 100 | H | H | CH₃ | CH₃ | CH₃ | CH₂ | 4-CN | Pinkish powder | 234–237 |
| 101 | H | H | CH₃ | CH₃ | CH₃ | CH₂ | 2,4,6-(CH₃)₃ | White powder | 228–235 |
| 102 | H | H | CH₃ | CH₃ | CH₃ | CH₂ | 2,3,4,5,6-F₅ | White powder | 180–181 |
| 103 | H | H | CH₃ | CH₃ | CH₃ | CH₂ | 4-OC₂H₅ | Milky white powder | 179–180 |
| 104 | H | H | CH₃ | CH₃ | CH₃ | CH₂ | 4-OCH₃ | White crystals | 165–168 |
| 105 | H | H | CH₃ | CH₃ | CH₃ | CH₂ | 4-C₂H₅ | Milky white powder | 205–212 |
| 106 | H | H | CH₃ | CH₃ | CH₃ | CH₂ | 4-NO₂ | Milky white powder | 217–221 |
| 107 | H | H | CH₃ | CH₃ | C₂H₅ | CH₂ | 3,4-Cl | Milky white crystals | 185–187 |
| 108 | H | H | CH₃ | CH₃ | C₂H₅ | CH₂ | 3-CF₃ | Light brownish crystals | 107–108 |
| 109 | H | H | CH₃ | CH₃ | n-C₃H₇ | CH₂ | 3,4-Cl₂ | Milky white crystals | 210–213 |
| 110 | H | H | CH₃ | CH₃ | i-C₃H₇ | CH₂ | 3,4-Cl₂ | White crystals | 235–240 |
| 111 | H | H | CH₃ | CH₃ | i-C₃H₇ | CH₂ | 4-Cl | White crystals | 222–223 |
| 112 | H | H | H | H | H | —CH(CH₃)— | 4-Cl | White crystals | 208–209 |
| 113 | H | H | H | H | H | —CH(CH₃)— | 3-Cl | White crystals | 160–162 |
| 114 | H | H | H | H | H | —CH(CH₃)— | 3,4-Cl₂ | White crystals | 233–236 |
| 115 | H | H | H | H | H | —(CH₂)₂— | 4-Cl | Milky white crystals | 193–196 |
| 116 | H | H | H | H | CH₃ | —(CH₂)₂— | H | Colorless powder | 184–185 |
| 117 | H | H | H | H | CH₃ | —(CH₂)₂— | 4-Cl | Colorless powder | 195–197 |
| 118 | H | H | H | H | CH₃ | —(CH₂)₂— | 4-CH₃ | Light yellow powder | 197–198 |
| 119 | H | H | CH₃ | CH₃ | CH₃ | —(CH₂)₂— | H | Light yellow powder | 142–143 |
| 120 | H | H | CH₃ | CH₃ | CH₃ | —(CH₂)₂ | 4-Cl | Light yellow powder | 193–195 |
| 121 | H | H | H | H | H | —C(CH₃)₂— | 3-Cl | White powder | 249–256 |
| 122 | H | H | H | H | H | —C(CH₃)₂— | 2-Cl | White crystals | 255–258 |
| 123 | H | H | H | H | H | —C(CH₃)₂— | 4-Cl | White crystals | 240–244 |
| 124 | H | H | H | H | H | —C(CH₃)₂— | 2,4-Cl₂ | Milky white crystals | 250–253 |
| 125 | H | H | H | H | CH₃ | —C(CH₃)₂— | 2-Cl | Milky white crystals | 242–244 |

-continued

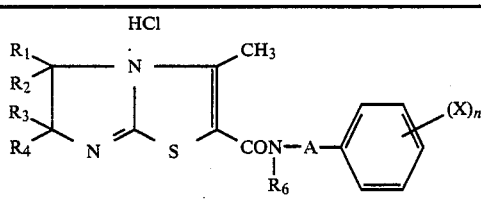

| Compound No. | $R_1$ | $R_2$ | $R_3$ | $R_4$ | $R_6$ | A | $X_n$ | Appearance | Melting point (°C.) |
|---|---|---|---|---|---|---|---|---|---|
| 126 | H | H | $CH_3$ | $CH_3$ | H | $-C(CH_3)_2-$ | 2-Cl | White crystals | 212–216 |
| 127 | H | H | $CH_3$ | $CH_3$ | H | $-C(CH_3)_2-$ | 4-Cl | Light yellowish flaky crystals | 170–172 |
| 128 | H | H | $CH_3$ | $CH_3$ | H | $-C(CH_3)_2-$ | 2,4-$Cl_2$ | White crystals | 240–246 |
| 129 | H | H | $CH_3$ | $CH_3$ | H | $-C(CH_3)_2-$ | 3-Cl | Milky white crystals | 119–125 |
| 130 | H | H | $CH_3$ | $CH_3$ | $CH_3$ | $-C(CH_3)_2-$ | 2-Cl | White crystals | 255–257 |
| 131 | H | H | H | H | H (cyclopentyl) | $-C(CH_3)_2-$ | 4-Cl | White down-like crystals | 215–220 |
| 132 | H | H | $CH_3$ | $CH_3$ | H (cyclopentyl) | $-C(CH_3)_2-$ | 4-Cl | White down-like crystals | 250–253 |
| 133 | H | H | H | H | H | $CH_2$ | 3,4-$Cl_2$ | White down-like crystals | 206–207 |

Referential Example 3:

Dissolved in toluene were 2.5 g (0.02 mole) of m-chloroaniline and a catalytic amount of pyridine, followed by dropwise addition of 1.9 g (0.022 mole) of diketene at 50° C. After completion of the dropwise addition, the resultant mixture was heated under reflux for 3 hours. Under ice-cooling, ligroin was added, and precipitated crystals were collected by filtration and were then washed first with ligroin and then with hexane. The crystals were then dried under reduced pressure to obtain 3'-chloroacetoacetanilide.

Example 134:

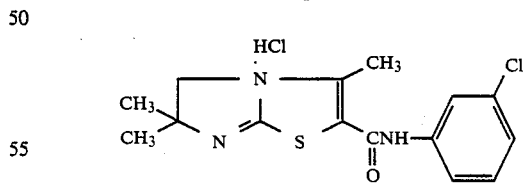

(i) Dissolved in diethyl ether was 2.1 g (0.01 mole) of the 3'-chloroacetanilide obtained in Referential Example 3, followed by a dropwise addition of 1.5 g (0.011 mole) of sulfuryl chloride at −5° C. The resultant mixture was stirred at −10—−5° C. for 30 minutes. The reaction mixture was poured into ice water, neutralized with sodium hydrogencarbonate and then extracted with toluene. The organic layer was dried and concentrated. The residue was dissolved in methyl ethyl ketone, followed by an addition of 1.3 g (0.01 mole) of 4,4-dimethylimidazolidine-2-thione. The mixture was heated under reflux for 3 hours. Precipitated crystals were collected by filtration, recrystallized from isopropanol, and then dried at 120° C. under reduced pressure for 3 hours. The crystals were then suspended in methyl ethyl ketone and heated under reflux for 20 hours. The reaction mixture was cooled, and the resultant precipitate was collected by filtration, washed with acetone and then dried under reduced pressure to obtain 2.6 g of 3'-chloro-3,6,6-trimethyl-5,6-dihydroimidazo[2,1-b]thiazole-2-carboxyanilide hydrochloride (Compound 134) [yield: 72.2%].

PMR ppm δ (DMSO-d₆): 1.53 (6H,s,6.6(CH₃)₂), 2.53 (3H,s,3—CH₃), 4.27 (2H,s,5—CH₂—), 7.03–8.00 (4H,m,aromatic proton), 10.80 (1H,s,—NH—).

(ii) Dissolved in water was 1.8 g (0.005 mole) of the thus-obtained 3'-chloro-3,6,6-trimethyl-5,6-dihydroimidazo[2,1-b]thiazole-2-carboxyanilide hydrochloride. While stirring the aqueous solution at room temperature, a 20% aqueous solution of potassium carbonate was added dropwise. The resultant precipitate was collected by filtration and then washed and purified with a great deal of water. The precipitate was then dried under reduced pressure to obtain 1.3 g of 3'-chloro-3,6,6-trimethyl-5,6-dihydroimidazo[2,1-b]thiazole-2-carboxyanilide (melting point: 172°–173° C.; milky white powder).

Example 135:

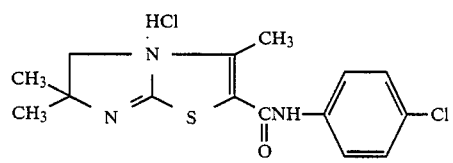

(i) Dissolved in diethyl ether was 2.1 g (0.01 mole) of 4'-chloroacetanilide obtained in the same manner as in Referential Example 3, followed by a dropwise addition of 1.5 g (0.011 mole) of sulfuryl chloride at −5° C. The resultant mixture was stirred at −10°−−5° C. for 30 minutes. The reaction mixture was poured in ice water, neutralized with sodium hydrogencarbonate and then extracted with toluene. The organic layer was dried and concentrated. The residue was dissolved in methyl ethyl ketone, followed by an addition of 1.3 g (0.01 mole) of 4,4-dimethylimidazolidine-2-thione. The mixture was heated under reflux for 3 hours. Precipitated crystals were collected by filtration, washed with acetone and then dried under reduced pressure to obtain 3.4 g of 4'-chloro-3,6,6-trimethyl-5,6-dihydroimidazo[2,1-b]thiazole-2-carboxyanilide hydrochloride (Compound 135) [yield: 94.4%].

Melting point: 264°–268° C.

(ii) Dissolved in water was 1.8 g (0.005 mole) of the thus-obtained 4'-chloro-3,6,6-trimethyl-5 6-dihydroimldazo[2,1-b]thiazole-2-carboxyanilide hydrochloride. While stirring the aqueous solution at room temperature, a 10% aqueous solution of caustic soda was added dropwise. The resultant precipitate was collected by filtration and then washed and purified with a great deal of water. The precipitate was then dried under reduced pressure to obtain 1.0 g of 4'-chloro-3,6,6-trimethyl-5,6-dihydroimidazo[2,1-b]-thiazole-2-carboxyanilide (melting point: 235°–236° C.; white powder).

Example 136:

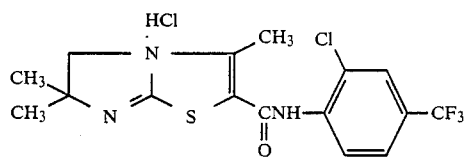

(i) Dissolved in carbon tetrachloride were 2.8 g (0.01 mole) of 2'-chloro-4'-trifluoromethylacetoacetanilide obtained in the same manner as in Referential Example 3 and 1.4 g (0.0 mole) of N-chlorosuccinimide, followed by an addition of a small amount of benzoyl peroxide. The resultant suspension was heated under reflux for 1 hour. The reaction mixture was washed with water, dried and then concentrate.. The residue was dissolved in methyl ethyl ketone, followed by an addition of 1.3 g (0.01 mole) of 4,4-dimethyl-imidazolidine-2-thione. The mixture was heated under reflux for 3 hours. Precipitated crystals were collected by filtration, recrystallized from isopropyl ether-ethanol and then dried at 120° C. under reduced pressure for 3 hours to obtain 2.5 g of 2'-chloro-4'-trifluoromethyl-3,6,6-trimethyl-5,6-dihydroimidazo-[2,1-b]thiazole-2-carboxyanilide hydrochloride (Compound 136) [yield: 61.9%].

Melting point: 148°–150° C.

Example 137:

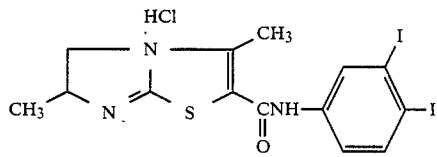

Dissolved in carbon tetrachloride were 4.3 g (0.01 mole) of 3',4'-diiodoacetoacetanilide obtained in the same manner as in Referential Example 3 and 1.4 g (0.01 mole) of N-chlorosuccinimide, followed by an addition of a small amount of benzoyl peroxide. The resultant suspension was heated under reflux for 1 hour. The reaction mixture was washed with water, dried and then concentrated. The residue was dissolved in methyl ethyl ketone, followed by an addition of 1.2 g (0.01 mole) of 4-methylimidazolidine-2-thione. The mixture was heated under reflux for 3 hours. Precipitated crystals were collected by filtration, washed with acetone and then dried under reduced pressure to obtain 4.8 g of 3',4'-diiodo-3,6-dimethyl-5,6-dihydroimidazo[2,1-b]thiazole-2-carboxyanilide hydrochloride (Compound 137) [yield: 85.7%].

Melting point: 278°–280° C.

Example 138:

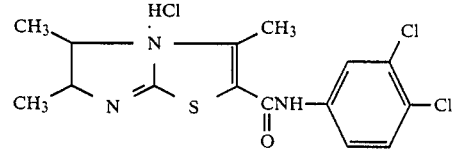

Dissolved in carbon tetrachloride were 2.5 g (0.01 mole) of 3',4'-diiodoacetoacetanilide obtained in the same manner as in Referential Example 3 and 1.4 g (0.01 mole) of N-chlorosuccinimide, followed by an addition of a small amount of benzoyl peroxide. The resultant suspension was heated under reflux for 1 hour. The reaction mixture was washed with water, dried and then concentrate. The residue was dissolved in methyl ethyl ketone, followed by an addition of 1.3 g (0.01 mole) of 4,5-dimethylimidazolidine-2-thione. The mixture was heated under reflux for 3 hours. Precipitated crystals were collected by filtration, recrystallized from isopropyl ether-ethanol, and the dried at 120° C. under reduced pressure for 3 hours to obtain 2.5 g of 3',4'-dichloro-3,5,6-trimethyl-5,6-dihydroimidazo[2,1-b]thiazole-2-carboxyanilide hydrochloride (Compound 138) [yield: 64.1%].

Melting point: 240°–245° C.

Examples 139–171:

The following compounds were obtained in the same manner as in Referential Example 3 and Examples 134–138.

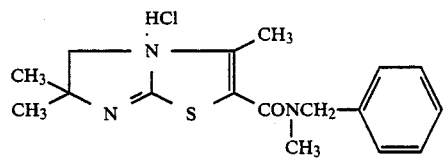

(m.p.: 140°–142° C.; white powder)
Compound 173:

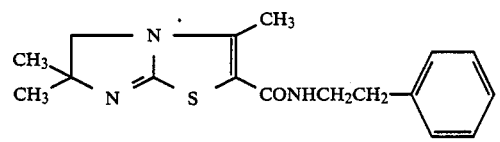

(m.p.: 102°–105° C.; slightly brown powder)
Compound 174:

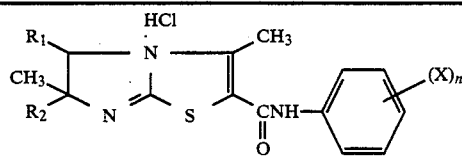

| No. | $R_1$ | $R_2$ | $X_n$ | Appearance | Melting point (°C.) |
|---|---|---|---|---|---|
| 139 | H | H | H | Yellowish powder | 207–209 |
| 140 | H | H | 2-Cl | White powder | 205–212 |
| 141 | H | H | 3-Cl | White powder | 196–198 |
| 142 | H | H | 4-Cl | Yellowish powder | 240–244 |
| 143 | H | H | 2,4-$Cl_2$ | White powder | 245–253 |
| 144 | H | H | 3,4-$Cl_2$ | Yellowish powder | 234–235 |
| 145 | H | H | 3,5-$Cl_2$ | Yellowish powder | 255–259 |
| 146 | H | H | 3-Br | White powder | 201–204 |
| 147 | H | H | 4-$NO_2$ | Light yellowish powder | 255–258 |
| 148 | H | H | 3-I | White powder | 203–204 |
| 149 | H | H | 4-I | White powder | 270 |
| 150 | H | H | 2-$CH_3$ | White powder | 241–246 |
| 151 | H | H | 4-$CH_3$ | Milky white powder | 208–210 |
| 152 | H | H | 2-$OCH_3$ | White powder | 245–253 |
| 153 | H | H | 4-$OCH_3$ | White powder | 210–215 |
| 154 | H | H | 3-$OC_3H_7$-i | White powder | 115–122 |
| 155 | H | H | 2-Cl, 4-$CF_3$ | White powder | 138–142 |
| 156 | H | H | 3-Cl, 4-F | Gray powder | 150–154 |
| 157 | $CH_3$ | H | 3,4-$I_2$ | Brown powder | 214–215 |
| 158 | $CH_3$ | H | 4-Cl | White powder | 259–264 |
| 159 | $CH_3$ | H | 2-Cl, 4-$CF_3$ | White flaky crystals | 178–182 |
| 160 | H | $CH_3$ | 3,4-$Cl_2$ | Brown syrupy matter | 128–136 |
| 161 | H | $CH_3$ | 2,4-$Cl_2$ | Light orange crystals | 172–175 |
| 162 | H | $CH_3$ | 3,5-$Cl_2$ | Yellowish crystals | 155–160 |
| 163 | H | $CH_3$ | 3,4-$I_2$ | Light brownish crystals | 266–268 |
| 164 | H | $CH_3$ | 4-I | White crystals | 220–225 |
| 165 | H | $CH_3$ | 3-Cl, 4-F | Gray powder | 251–256 |
| 166 | H | $CH_3$ | 3,5-$(CF_3)_2$ | Gray powder | 261–265 |
| 167 | H | $CH_3$ | H | White crystals | 240–245 |
| 168 | H | $CH_3$ | 4-Br | White crystals | 255–261 |
| 169 | H | $CH_3$ | 2,5-$(OCH_3)_2$ | Milky white powder | 245–247 |
| 170 | H | $CH_3$ | 2-$OCH_3$, 5-OH | Yellowish brown powder | 279–281 |
| 171 | H | $CH_3$ | 3-Cl, 4-OH | Brown powder | 272–273 |

Examples 172–174:

The following compounds were prepared in the same manner as in Referential Example 2 and Example 44.
Compound 172:

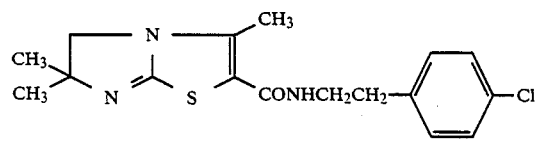

(m.p.: 171°–174° C.; slightly yellow powder)

Having now fully described the invention, it will be apparent to one of ordinary skill in the art that many changes and modifications can be made thereto without departing from the spirit or scope of the invention as set forth herein.

We claim:

1. A 5,6-dihydroimidazo[2,1-b]thiazole-2-carboxamide derivative represented by the following general formula [I]

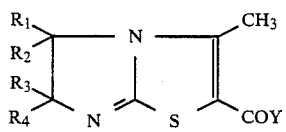

wherein $R_1$, $R_2$, $R_3$ and $R_4$ are either the same or different and mean individually a hydrogen atom or lower alkyl group, Y denotes a group of the following formula:

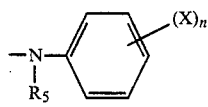

wherein $R_5$ means a lower alkyl group, X denotes a hydrogen or halogen atom or a trifluoromethyl, lower alkyl, lower alkoxy or nitro group, n stands for an integer of 0–5, and when n is greater than 1, Xs are either the same or different;

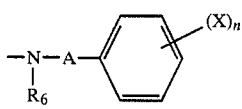

wherein A means a lower alkylene group which may be branched, $R_6$ denotes a hydrogen atom or a lower alkyl or cycloalkyl group, and X and n have the same meaning as defined above;

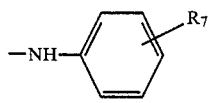

wherein $R_7$ means a hydrogen, chlorine, bromine or iodine atom or a lower alkyl, lower alkoxy or nitro group; or

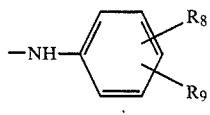

wherein $R_8$ means a halogen atom or a lower alkoxy or trifluoromethyl group and $R_9$ denotes a halogen atom or a hydroxyl, lower alkoxy or trifluoromethyl group), with a proviso that at least one of $R_1$, $R_2$, $R_3$ and $R_4$ is a methyl group when the group Y is

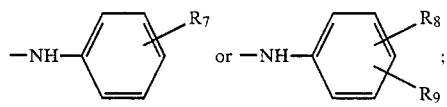

or a salt thereof.

2. A 5,6-dihydroimidazo[2,1-b]thiazole-2-carboxamide derivative as claimed in claim 1, wherein Y denotes a group of the following formula:

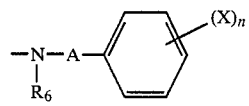

wherein A means a lower alkylene group which may be branched, $R_6$ denotes a hydrogen atom or a lower alkyl or cycloalkyl group, and X and n have the same meaning as defined in claim 1.

3. A 5,6-dihydroimidazo[2,1-b]thiazole-2-carboxamid derivative as claimed in claim 1, wherein either one of $R_2$ and $R_4$ is a hydrogen atom and the other is a methyl group; and Y denotes a group of the following formula:

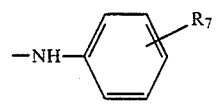

wherein $R_7$ means a hydrogen, chlorine, bromine or iodine atom or a lower alkyl, lower alkoxy or nitro group; or

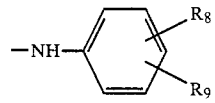

wherein $R_8$ means a halogen atom or a lower alkoxy or trifluoromethyl group and $R_9$ denotes a halogen atom or a hydroxy, lower alkoxy or trifluoromethyl group.

4. A 5,6-dihydroimidazo[2,1-b]thiazole-2-carboxamide derivative as claimed in claim 1, wherein Y denotes a group of the following formula:

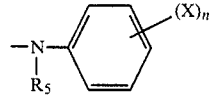

wherein $R_5$ means a lower alkyl group, X denotes a hydrogen or halogen atom or a trifluoromethyl, lower alkyl, lower alkoxy or nitro group, n stands for an integer of 0–5, and when n is greater than 1, Xs are either the same or different.

5. A 5,6-dihydroimidazo[2,1-b]thiazole-2-carboxamide derivative as claimed in claim 1, wherein $R_2$ means a hydrogen atom and Y denotes a group of the following formula:

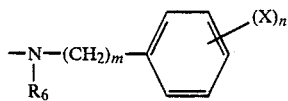

wherein m stands for an integer of 1–3, and $R_6$, X and n have the same meaning as defined in claim 1.

6. A 5,6-dihydroimidazo[2,1-b]thiazole-2-carboxamide derivative as claimed in claim 1, wherein $R_2$ means a hydrogen atom, $R_4$ stands for a methyl group, and Y denotes a group of the following formula:

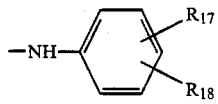

wherein $R_{17}$ and $R_{18}$ may be either the same of different and mean individually a hydrogen or chlorine or iodine atom or a trifluoromethyl group, with a proviso that $R_{18}$ is other than a trifluoromethyl group when $R_{17}$ is a hydrogen atom.

7. A 5,6-dihydroimidazo[2,1-b]thiazole-2-carboxamide derivative as claimed in claim 1, wherein $R_1$ and $R_2$ are both hydrogen atoms and Y denotes a group of the following formula:

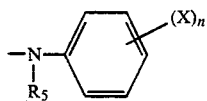

wherein $R_5$, X and n have the same meaning as defined in claim 1.

8. A 5,6-dihydroimidazo[2,1-b]thiazole-2-carboxamide derivative as claimed in claim 1, wherein $R_1$, $R_2$, $R_3$ and $R_4$ mean individually a hydrogen atom and Y denotes a group of the following formula:

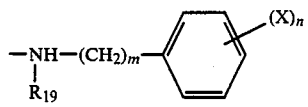

wherein $R_{19}$ means a hydrogen or alkyl group having 1–3 carbon atoms, m stands for an integer of 1–3, and X and n have the same meaning as defined above.

9. A 5,6-dihydroimidazo[2,1-b]thiazole-2-carboxamide derivative as claimed in claim 1, wherein $R_1$ and $R_2$ mean individually a hydrogen atom, $R_3$ and $R_4$ denote individually a methyl group, and Y is a group of the following formula:

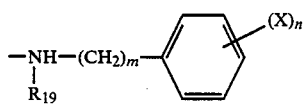

wherein $R_{19}$ means a hydrogen atom or alkyl group having 1–3 carbon atoms, m stands for an integer of 1–3, and X and n have the same meaning as defined above.

10. A 5,6-dihydroimidazo[2,1-b]thiazole-2-carboxamide derivative as claimed in claim 1, wherein $R_1$ and $R_3$ mean individually a methyl group, $R_2$ and $R_4$ denote individually a hydrogen atom, and Y is a group of the following formula:

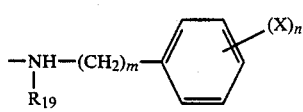

wherein $R_{19}$ means a hydrogen atom or alkyl group having 1–3 carbon atoms, m stands for an integer of 1–3, and X and n have the same meaning as defined above.

* * * * *

UNITED STATES PATENT AND TRADEMARK OFFICE
CERTIFICATE OF CORRECTION

PATENT NO. : 4,910,315

DATED : MARCH 20, 1990

INVENTOR(S) : Itaru YAMAMOTO et al

It is certified that error appears in the above-identified patent and that said Letters Patent is hereby corrected as shown below:

On the title page, in item [54], the Title should read:

-- 5,6-DIHYDROIMIDAZO[2,1-b]THIAZOLE-2-CARBOXAMIDE DERIVATIVES OR SALTS THEREOF --.

Signed and Sealed this

Third Day of March, 1992

Attest:

HARRY F. MANBECK, JR.

*Attesting Officer*   *Commissioner of Patents and Trademarks*